US012745950B2

(12) United States Patent
Antoine et al.

(10) Patent No.: US 12,745,950 B2
(45) Date of Patent: Sep. 29, 2026

(54) HYPERHIDROSIS DIAGNOSTIC DEVICE AND METHOD

(71) Applicant: 11025368 CANADA INC., Montréal (CA)

(72) Inventors: Cassandre Antoine, Montreal (CA); Rahma Assiani, Montreal (CA); Maxime Calouche, Montreal (CA); Noémie Candau, Montreal (CA); Nicolas Jolicoeur, Montreal (CA); Anika Tremblay-Robert, Montreal (CA)

(73) Assignee: 11025368 CANADA INC., Montreal (CA)

( * ) Notice: Subject to any disclaimer, the term of this patent is extended or adjusted under 35 U.S.C. 154(b) by 431 days.

(21) Appl. No.: 18/579,484

(22) PCT Filed: Jul. 14, 2022

(86) PCT No.: PCT/CA2022/051099
§ 371 (c)(1),
(2) Date: Jan. 15, 2024

(87) PCT Pub. No.: WO2023/283741
PCT Pub. Date: Jan. 19, 2023

(65) Prior Publication Data

US 2024/0341673 A1 Oct. 17, 2024

Related U.S. Application Data

(60) Provisional application No. 63/221,696, filed on Jul. 14, 2021.

(51) Int. Cl.
*A61B 5/00* (2006.01)
*A61B 5/01* (2006.01)

(52) U.S. Cl.
CPC .............. *A61B 5/4266* (2013.01); *A61B 5/01* (2013.01); *A61B 2562/029* (2013.01)

(58) Field of Classification Search
None
See application file for complete search history.

(56) References Cited

U.S. PATENT DOCUMENTS

2021/0353162 A1* 11/2021 Tan ...................... A61B 5/7275

* cited by examiner

*Primary Examiner* — Jay B Shah
(74) *Attorney, Agent, or Firm* — PRAXIS

(57) ABSTRACT

A device and method are provided for diagnosing hyperhidrosis or for use in the diagnosis of hyperhidrosis by capturing, collecting, and measuring a sweat sample on a skin surface of a subject. The device includes a sweat capturing and collecting body forming a cavity therein and defining an opening leading to the cavity and being circumscribed by a contact surface for engaging the skin surface. Engagement of the skin surface by the contact surface provides for sealing the cavity thereby forming a chamber for capturing and collecting the sweat sample. A humidity sensor positioned within the cavity measures humidity within the chamber which corresponds to a sweat rate measurement. A temperature sensor positioned within the cavity measures temperature within the chamber which corresponds to a skin temperature measurement. A controller is in operative communication with the humidity sensor and the temperature sensor for receiving the measured humidity and temperature within the chamber. A user interface is in operative communication with the controller for communicating the measured humidity and temperature within the chamber.

22 Claims, 6 Drawing Sheets

HYPERHIDROSIS DIAGNOSTIC DEVICE AND METHOD

CROSS-REFERENCE TO RELATED APPLICATIONS

The present application claims priority on U.S. Provisional Patent Application Ser. No. 63/221,696 filed on Jul. 14, 2021.

TECHNICAL FIELD

The present disclosure generally relates to hyperhidrosis. More particularly, but not exclusively, the present disclosure relates to a hyperhidrosis diagnostic device and method. Still more particularly, yet still not exclusively, the present disclosure relates to a device and a method for capturing, collecting, and measuring a sweat sample on a skin surface of a subject.

BACKGROUND

Hyperhidrosis is abnormally excessive sweating that is not necessarily related to heat or exercise. To diagnose this condition, a clinician examines a patient looking closely at the areas of the body that sweat excessively. The clinician will also ask specific questions to understand why the patient has or believes they have excessive sweating. A dermatologist also asks very specific questions. This helps the doctor understand why the patient has excessive sweating. This diagnosis requires the cognitive cooperation of the patient and as such can be subjective.

A variety of devices and methods for objectively measuring excessive sweat have been provided, including: methods and devices for evoking and measuring a sweat response; methods and devices for measuring TEWL (TransEpidermal Water Loss); methods and devices for assessing the response of patients with primary palmoplantar hyperhidrosis to bilateral thoracoscopic sympathectomy in order to evaluate symptoms and sweat production. The state of art also teaches a wearable sweat sensing device configured to be placed on a wearer's skin and capable of volumetrically determining sweat rate. Moreover, methods and apparatuses have also been provided for quantitatively measuring the amount of transepidermal water loss as well as convection heat emitted from a skin surface by diffusion.

OBJECTS

An object of the present disclosure is to provide a hyperhidrosis diagnostic device.

An object of the present disclosure is to provide a device for use in diagnosis of hyperhidrosis.

An object of the present disclosure is to provide a device for capturing, collecting, and measuring a sweat sample on a skin surface of a subject.

An object of the present disclosure is to provide a hyperhidrosis diagnostic method.

An object of the present disclosure is to provide a method for capturing, collecting and measuring a sweat sample on a skin surface of a subject.

SUMMARY

In accordance with an aspect of the present disclosure, there is provided a device for capturing, collecting, and measuring a sweat sample on a skin surface of a subject, the device comprising: a sweat capturing and collecting body forming a cavity therein and defining an opening leading to the cavity and being circumscribed by a contact surface for engaging the skin surface, wherein engagement of the skin surface by the contact surface provides for sealing the cavity thereby forming a chamber for capturing and collecting the sweat sample; a humidity sensor positioned within the cavity for measuring humidity within the chamber which corresponds to a sweat rate measurement; a temperature sensor positioned within the cavity for measuring temperature within the chamber which corresponds to a skin temperature measurement; a controller in operative communication with the humidity sensor and the temperature sensor for receiving the measured humidity and temperature within the chamber; and a user interface in operative communication with the controller for communicating the measured humidity and temperature within the chamber.

In an embodiment, the device further comprises an ambient humidity sensor for measuring ambient humidity and being in operative communication with the controller for receiving the measured ambient humidity and for determining a humidity gradient between the measured ambient humidity and the measured humidity within the chamber. In an embodiment, the ambient humidity sensor is positioned externally of the chamber. In an embodiment, the ambient humidity sensor is positioned on an external surface of the sweat capturing and collecting body. In an embodiment, the ambient humidity sensor is positioned within the cavity. In an embodiment, the humidity gradient is communicated via the user interface.

In an embodiment, the device further comprises an ambient temperature sensor for measuring ambient temperature and being in operative communication with the controller for receiving the measured ambient temperature and for determining a temperature gradient between the measured ambient temperature and the measured temperature within the chamber. In an embodiment, the ambient temperature sensor is positioned externally of the chamber. In an embodiment, the ambient temperature sensor is positioned on an external surface of the sweat capturing and collecting body. In an embodiment, the ambient temperature sensor is positioned within the cavity. In an embodiment, the temperature gradient is communicated via the user interface.

In an embodiment, the device further comprises at least one additional sensor positioned within the cavity and in operative communication with the controller. In an embodiment, the at least one additional sensor is selected from the group consisting of: a heart rate sensor, an internal body temperature sensor, a pH sensor, a colorimetry sensor, a volatile organic compound sensor, a force measuring sensor and any combination thereof.

In an embodiment, the device further comprises an atmospheric pressure sensor positioned externally of the chamber and in operative communication with the controller. In an embodiment, the atmospheric pressure sensor is positioned on an external surface of the sweat capturing and collecting body. In an embodiment, the device further comprises an atmospheric pressure sensor positioned within the cavity and in operative communication with the controller.

In an embodiment, the chamber defines a configuration and size, the device further comprising a recognition system for recognizing the configuration and size of the chamber. In an embodiment, the recognition system is positioned within the cavity. In an embodiment, the recognition system is in operative communication with the controller.

In an embodiment, the device further comprises a handle connected to a sweat capturing and collecting body. In an embodiment, the handle houses the controller. In an embodiment, the handle comprises the user interface. In an embodiment, the user interface comprises a display. In an embodiment, the device further comprises a housing positioned within the cavity. In an embodiment, the housing provides for housing an element selected from the group consisting of the humidity sensor, temperature sensor, the controller and any combination thereof.

In accordance with an aspect of the present disclosure, there is provided a device for diagnosing hyperhidrosis or for use in the diagnosis of hyperhidrosis comprising: a sweat capturing and collecting body forming a cavity therein and defining an opening leading to the cavity and being circumscribed by a contact surface for engaging the skin surface, wherein engagement of the skin surface by the contact surface provides for sealing the cavity thereby forming a chamber for capturing and collecting the sweat sample; an internal humidity sensor positioned within the cavity for measuring internal humidity within the chamber which corresponds to a sweat rate measurement; an internal temperature sensor positioned within the cavity for measuring internal temperature within the chamber which corresponds to a skin temperature measurement; an ambient humidity sensor for measuring ambient humidity in an ambient environment to the skin; an ambient temperature sensor for measuring ambient temperature in an ambient environment to the skin; a user interface; a controller in operative communication with the internal humidity sensor, the internal temperature sensor, the ambient humidity sensor, the ambient temperature sensor, and the user interface, the controller comprising a memory of controller executable code that when executed provides the controller with performing controller executable steps comprising: receiving the measured internal humidity within the chamber from the internal humidity sensor at an initial time stamp and at a final time stamp; receiving the measured internal temperature within the chamber from the internal temperature sensor at the initial time stamp and the final time stamp; determining an initial molecular concentration of water in the air of the chamber at the initial time stamp and a final molecular concentration of water in air of the chamber at the final time stamp based on the internal humidity and internal temperature at the initial time stamp and the final time stamp respectively by performing calculations steps stored within the memory; determining a molecular concentration gradient between the initial and final molecular concentrations of water in the air of the chamber; receiving the measured ambient humidity from the ambient humidity sensor at the initial time stamp; receiving the measured ambient temperature from the ambient temperature sensor at the initial time stamp; modulating the internal molecular concentration gradient based on the ambient humidity and ambient temperature at the initial time stamp by performing modulation steps stored within the memory thereby determining a modulated molecular concentration gradient; comparing the modulated molecular concentration gradient to a hyperhidrosis level and molecular concentration gradient correspondence table stored within the memory thereby determining a hyperhidrosis condition; and communicating the determined hyperhidrosis condition via the user interface.

In an embodiment, the ambient humidity sensor is positioned externally to the chamber or within the cavity. In an embodiment, the ambient temperature sensor is positioned externally to the chamber or within the cavity.

In an embodiment, the device comprises an atmospheric pressure sensor in operative communication with the controller for measuring atmospheric pressure, wherein the controller executable steps further comprise: receiving the measured atmospheric pressure, and wherein the analysis steps comprise modulating the molecular concentration gradient based on the measured atmospheric pressure.

In an embodiment, the device comprises a heart rate sensor for measuring the heart rate of the subject and being in operative communication with the controller, wherein the controller executable steps further comprise: receiving the measured heart rate, and wherein the analysis steps comprises modulating the molecular concentration gradient based on the measured heart rate.

In an embodiment, the device further comprises a body temperature sensor for measuring the internal body temperature of the subject and being in operative communication with the controller, wherein the controller executable steps further comprise: receiving the measured internal body temperature, and wherein the analysis steps comprises modulating the molecular concentration gradient based on the measured internal body temperature.

In accordance with an aspect of the present disclosure, there is provided a device for diagnosing hyperhidrosis or for use in the diagnosis of hyperhidrosis comprising: a sweat capturing and collecting body forming a cavity therein and defining an opening leading to the cavity and being circumscribed by a contact surface for engaging the skin surface, wherein engagement of the skin surface by the contact surface provides for sealing the cavity thereby forming a chamber for capturing and collecting the sweat sample; an internal humidity sensor positioned within the cavity for measuring internal humidity within the chamber which corresponds to a sweat rate measurement; an internal temperature sensor positioned within the cavity for measuring internal temperature within the chamber which corresponds to a skin temperature measurement; an ambient humidity sensor for measuring ambient humidity in an ambient environment to the skin; an ambient temperature sensor for measuring ambient temperature in an ambient environment to the skin; a user interface; a controller in operative communication with the internal humidity sensor, the internal temperature sensor, the ambient humidity sensor, the ambient temperature sensor, and the user interface, the controller comprising a memory of controller executable code that when executed provides the controller with performing controller executable steps comprising: receiving the measured internal humidity within the chamber from the internal humidity sensor at an initial time stamp and at a final time stamp; receiving the measured internal temperature within the chamber from the internal temperature sensor at the initial time stamp and the final time stamp; determining an initial specific humidity measurement in the chamber at the initial time stamp and a final specific humidity measurement in the chamber at the final time stamp based on the internal humidity and internal temperature at the initial time stamp and the final time stamp respectively by performing calculations steps stored within the memory; determining a specific humidity gradient between the determined initial specific humidity and determined final specific humidity; receiving the measured ambient humidity near the skin from the ambient humidity sensor at the initial time stamp; receiving the measured ambient temperature near the skin from the ambient temperature sensor at the initial time stamp; modulating the specific humidity gradient based on the ambient humidity and ambient temperature at the initial time stamp by performing modulation steps stored within the memory thereby determining a modulated specific humidity gradient; comparing the modulated specific humidity gradient to a hyperhidrosis level and specific humidity gradient correspondence table stored within the memory thereby determining a hyperhidrosis condition; and communicating the determined hyperhidrosis condition via the user interface.

In an embodiment, the ambient humidity sensor is positioned externally to the chamber or within the cavity. In an embodiment, the ambient temperature sensor is positioned externally to the chamber or within the cavity.

In an embodiment, the device further comprises an atmospheric pressure sensor in operative communication with the controller for measuring atmospheric pressure, wherein the controller executable steps further comprise: receiving the measured atmospheric pressure, and wherein the analysis steps comprise modulating the specific humidity gradient based on the measured atmospheric pressure.

In an embodiment, the device further comprises a heart rate sensor for measuring the heart rate of the subject and being in operative communication with the controller, wherein the controller executable steps further comprise: receiving the measured heart rate, and wherein the analysis steps comprises modulating the specific humidity gradient based on the measured heart rate.

In an embodiment, the device further comprises a body temperature sensor for measuring the internal body temperature of the subject and being in operative communication with the controller, wherein the controller executable steps further comprise: receiving the measured internal body temperature, and wherein the analysis steps comprise modulating the specific humidity gradient based on the measured internal body temperature.

In accordance with an aspect of the present disclosure, there is provided a method of diagnosing hyperhidrosis or for use in the diagnosis of hyperhidrosis by capturing, collecting and measuring a sweat sample on a skin surface of a subject, the method comprising: forming a sealed chamber on the skin surface for capturing and collecting the sweat sample; measuring internal humidity within the chamber at an initial time stamp and at a final time stamp; measuring internal temperature within the chamber at the initial time stamp and the final time stamp; determining an initial molecular concentration of water in the air of the chamber at the initial time stamp and a final molecular concentration of water in air of the chamber at the final time stamp based on the internal humidity and internal temperature at the initial time stamp and the final time stamp respectively; determining a molecular concentration gradient between the initial and final molecular concentrations of water in the air of the chamber; measuring ambient humidity in an ambient environment to the skin at the initial time stamp; measuring ambient temperature in an ambient environment the skin at the initial time stamp; modulating the internal molecular concentration gradient based on the ambient humidity and ambient temperature at the initial time stamp thereby determining a modulated molecular concentration gradient; comparing the modulated molecular concentration gradient to a hyperhidrosis level and molecular concentration gradient correspondence table thereby determining a hyperhidrosis condition.

In an embodiment, the method further comprises measuring atmospheric pressure in an ambient environment to the skin surface, wherein modulating the internal molecular concentration gradient is based on the measured atmospheric pressure.

In an embodiment, the method further comprises measuring an additional parameter selected from the group consisting of: a heart rate of the subject; a body temperature of the subject; a pH level in the chamber; a volatile organic compound concentration in the chamber; colorimetric analysis within the chamber; a force on the skin surface; and any combination thereof; wherein modulating the molecular concentration gradient is based on one or more of the additional parameters.

In an embodiment, the method further comprises: recognizing a configuration and size of the chamber; wherein modulating the molecular concentration gradient is based on the recognized configuration and size of the chamber.

In an embodiment, the method provides for evaluating hyperhidrosis variation over a period of time, the method comprising: determining the modulated molecular concentration gradient at a first measuring session thereby providing a first modulated molecular concentration gradient; determining the modulated molecular concentration gradient at a second measuring session thereby providing a second modulated molecular concentration gradient, wherein the first and second session are spaced apart over a period of one or more months; wherein one of the first and second modulated molecular concentration gradients was determined during a summertime period thereby providing a determined summertime gradient value and the other of the first and second modulated molecular concentration gradients was determined during a wintertime period thereby providing a determined wintertime gradient value; transposing the determined summertime gradient value to a transposed wintertime value by multiplying the determined summertime gradient value by an environmental factor or transposing the determined wintertime gradient value to a transposed summertime value by multiplying the determined wintertime gradient value by an environmental factor; and comparing the second modulated molecular concentration gradient to the first modulated molecular concentration gradient to determine an increase or decrease in the hyperhidrosis level, wherein when the first modulated molecular concentration comprises the determined summertime gradient value and the second modulated molecular concentration gradient comprises the determined wintertime value, the second modulated molecular concentration gradient is transposed to the transposed summertime value for comparison with the first modulated molecular concentration gradient, and wherein when the first modulated molecular concentration comprises the determined wintertime gradient value and the second modulated molecular concentration gradient comprises the determined summertime value, the second modulated molecular concentration gradient is transposed to the transposed wintertime value for comparison with the first modulated molecular concentration gradient.

In accordance with an aspect of the present disclosure, there is provided a method of diagnosing hyperhidrosis or for use in the diagnosis of hyperhidrosis by capturing, collecting and measuring a sweat sample on a skin surface of a subject, the method comprising: forming a sealed chamber on the skin surface for capturing and collecting the sweat sample; measuring internal humidity within the chamber at an initial time stamp and at a final time stamp; measuring internal temperature within the chamber at the initial time stamp and the final time stamp; determining an initial specific humidity of the chamber at the initial time stamp and a final specific humidity of the chamber at the final time stamp based on the internal humidity and internal temperature at the initial time stamp and the final time stamp respectively; determining a specific humidity gradient between the initial specific humidity and the final specific humidity; measuring ambient humidity in an ambient environment to the skin at the initial time stamp; measuring ambient temperature in an ambient environment to the skin at the initial time stamp; modulating the specific humidity gradient based on the ambient humidity and ambient temperature at the initial time stamp thereby determining a modulated specific humidity gradient; comparing the modulated specific humidity gradient to a hyperhidrosis level and specific humidity gradient correspondence table thereby determining a hyperhidrosis condition.

In an embodiment, the method further comprises measuring atmospheric pressure in an ambient environment to the skin surface, wherein modulating the internal molecular concentration gradient is based on the measured atmospheric pressure.

In an embodiment, the method further comprises measuring an additional parameter selected from the group consisting of: a heart rate of the subject; a body temperature of the subject; a pH level in the chamber; a volatile organic compound concentration in the chamber; colorimetric analysis within the chamber; and any combination thereof; wherein modulating the specific humidity gradient is based on one or more of the additional parameters.

In an embodiment, the method further comprises: recognizing a configuration and size of the chamber; wherein modulating the specific humidity gradient is based on the recognized configuration and size of the chamber.

In an embodiment, the method provides for evaluating hyperhidrosis variation over a period of time, the method comprising: determining the modulated molecular concentration gradient at a first measuring session thereby providing a first modulated molecular concentration gradient; determining the modulated molecular concentration gradient at a second measuring session thereby providing a second modulated molecular concentration gradient, wherein the first and second session are spaced apart over a period of one or more months; wherein one of the first and second modulated molecular concentration gradients was determined during a summertime period thereby providing a determined summertime gradient value and the other of the first and second modulated molecular concentration gradients was determined during a wintertime period thereby providing a determined wintertime gradient value; transposing the determined summertime gradient value to a transposed wintertime value by multiplying the determined summertime gradient value by an environmental factor or transposing the determined wintertime gradient value to a transposed summertime value by multiplying the determined wintertime gradient value by an environmental factor; and comparing the second modulated molecular concentration gradient to the first modulated molecular concentration gradient to determine an increase or decrease in the hyperhidrosis level, wherein when the first modulated molecular concentration comprises the determined summertime gradient value and the second modulated molecular concentration gradient comprises the determined wintertime value, the second modulated molecular concentration gradient is transposed to the transposed summertime value for comparison with the first modulated molecular concentration gradient, and wherein when the first modulated molecular concentration comprises the determined wintertime gradient value and the second modulated molecular concentration gradient comprises the determined summertime value, the second modulated molecular concentration gradient is transposed to the transposed wintertime value for comparison with the first modulated molecular concentration gradient.

Other objects, advantages and features of the present disclosure will become more apparent upon reading of the following non-restrictive description of illustrative embodiments thereof, given by way of example only with reference to the accompanying drawings.

DETAILED DESCRIPTION OF ILLUSTRATIVE EMBODIMENTS

Figure 1:
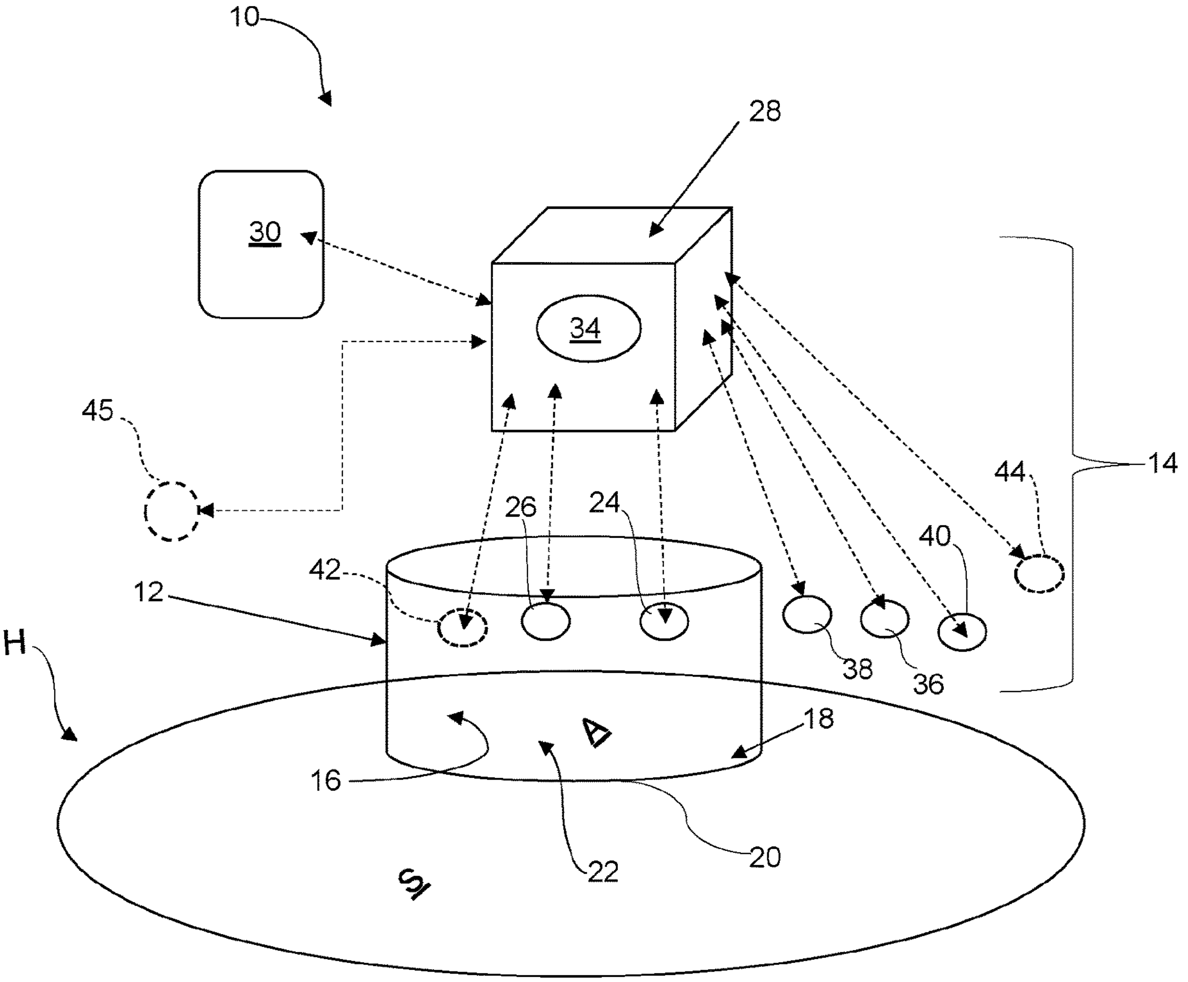
FIG. 1 is a schematic representation of a device for capturing, collecting and measuring a sweat sample on a skin surface of a subject in accordance with a non-limiting illustrative embodiment of the present disclosure.

Generally stated and in accordance with an aspect of the present disclosure, there is provided a device and method for capturing, collecting, and measuring a sweat sample on a skin surface of a subject. The device includes a sweat capturing and collecting body forming a cavity therein and defining an opening leading to the cavity and being circumscribed by a contact surface for engaging the skin surface. Engagement of the skin surface by the contact surface provides for sealing the cavity thereby forming a chamber for capturing and collecting the sweat sample. A humidity sensor positioned within the cavity measures humidity within the chamber which corresponds to a sweat rate measurement. A temperature sensor positioned within the cavity measures temperature within the chamber which corresponds to a skin temperature measurement. A controller is in operative communication with the humidity sensor and the temperature sensor for receiving the measured humidity and temperature within the chamber. A user interface is in operative communication with the controller for communicating the measured humidity and temperature within the chamber.

In an embodiment, and in accordance with an aspect of the present disclosure, there is provided a diagnostic device and method for diagnosing hyperhidrosis and for evaluating the severity of hyperhidrosis. The rate and volume of a subject's sweat output provides for evaluating a hyperhidrosis condition. Accordingly, a sweat sample is captured and collected from a selected skin surface of a subject in order to measure the sweat output rate and to assess, in a quantitative manner and on a real time basis, one or more parameters of the sample. One of the parameters is humidity which corresponds to the quantity of sweat secreted by the body over a period of time. Another parameter is air temperature of the region delimited by the device which corresponds to the temperature of the skin over a period of time. The parameter measurements are analyzed. The analyzed measurements provide for determining hyperhidrosis, a type of hyperhidrosis and a severity level thereof.

In an embodiment, the devices and methods herein use hygrometry to evaluate the volume of the sweat sample and the sweat production rate based on the humidity measurements. Transepidermal water loss provides for evaluating the severity of hyperhidrosis in agreement with controller implemented steps provided herein.

In accordance with an aspect of the present disclosure, there is provided a device providing along with a region of the skin surface a chamber for capturing and collecting a sweat sample therein to be measured by a sweat measurement and assessment arrangement including a sensor arrangement and a controller with an associated memory of controller executable code that when executed provides the controller with performing controller implementable steps including assessing and/or analyzing the sweat sample. The controller communicates the assessed/analyzed results via a user interface. The controller implementable steps and the method herein provide for determining hyperhidrosis in a subject, the type thereof, the severity level thereof.

With reference to FIG. 1, there is shown a device 10 for capturing, collecting, and measuring a sweat sample on a skin surface of a subject in accordance with a non-limiting illustrative embodiment of the present disclosure. In this non-restrictive illustrative embodiment, the device 10 comprises a sweat capturing and collecting body 12 and a sweat measuring and assessment arrangement, generally denoted 14.

The body 12 defines a cavity 16 and an opening 18 circumscribed by a contact surface 20. When the contact surface 20 engages a selected portion A of a skin surface S of a subject H, the cavity 16 is sealed thereby forming a chamber 22 for capturing and collecting the sweat sample.

The sweat measuring and assessment arrangement 14 comprises an internal humidity sensor 24 and an internal temperature sensor 26 and a controller 28 in operative communication with sensors 24 and 26. The controller 28 is also in operative communication with a user interface 30. The user interface 30 may include a display as well as an input interface for allowing the user to transmit control commands to the controller 28 in order to operate the sweat measuring arrangement 14.

The controller 28 comprises an associated memory 34 of controller executable code that when executed provides for the controller to perform controller implemented steps provided herein and including obtaining sweat measurements, analyzing the sweat measurements by performing calculations based on various parameters in order to determine if the sweat rate of the subject is excessive and/or diagnose hyperhidrosis, a type thereof as well as the severity thereof or to be used in the foregoing diagnosis The humidity sensor 24 is positioned within the cavity 16 so as to measure the humidity within the chamber 22 which corresponds to the sweat rate of the skin surface portion A. The temperature sensor 26 is positioned within the cavity 16 so as to measure the temperature within the chamber 22 which corresponds to temperature of the skin surface portion A. The sweat rate and temperature of the skin surface portion A are transmitted to the controller 28 and communicated to a device user via the user interface 30. Indeed, the sweat secreted by the skin surface portion A is captured and collected within the chamber 20 thereby modulating the humidity and temperature within the chamber 20 which is measured by the sensors 24 and 26.

In an embodiment, the device 10 comprises an ambient humidity sensor 36 and an ambient temperature sensor 38 positioned externally of the chamber 22 yet near the skin surface S for measuring the ambient humidity and ambient temperature in proximity to the skin surface S and to transmit this information to the controller 28 providing the controller 28 to determine, via execution of the controller 28 implementable steps, a gradient between the ambient humidity near the skin S and the humidity within the chamber 22 and a gradient between the ambient temperature near the skin S and the temperature within the chamber 22. These gradients or relative differentials are communicated to users via the user interface 30.

In an embodiment, the sweat measuring and assessment arrangement 14 of the device 10 comprises an atmospheric pressure sensor 40 positioned outside the chamber 22 and near the skin surface S in order to measure the atmospheric pressure ambient the skin surface S.

In an embodiment, the sweat measuring and assessment arrangement 14 of the device 10 comprises one or more additional internal sensors 42 within the chamber 22 including for example and without limitation to a heart rate sensor, an internal body temperature a pH sensor, a colorimetry sensor, a force measuring sensor, a volatile compound sensor and other suitable sensors including any combination thereof.

In an embodiment, the internal sensor 42 is part of a system of recognition of the size and/or shape of the chamber to modulate (i.e., attenuate, amplify etc.), via controller implementable steps, the measured parameters (via the sensors herein) that are dependent on the chamber volume, skin contact or a combination thereof to provide the controller additional entries of the analysis (via controller implementable steps) of the sweat sample independent of chamber size configuration and/or shape.

In an embodiment, the sweat measuring and assessment arrangement 14 of the device 10 comprises one or more additional ambient sensors 44 may also be provided outside of chamber 22 to measure other suitable ambient factors.

In an embodiment, the sweat measuring and assessment arrangement 14 of the device comprises the use of one or more additional sensors 45 for determining heart rate and internal body temperature.

The sensors 42 and 44 are in operative communication with the controller 28.

In an embodiment, sensors 45 are in operative communication with the controller 28.

The controller 28 provides for controlling and modulating the sensors of the sweat measuring and assessment arrangement 14, receiving measurements therefrom, analyzing and processing the measurements in order to communicate analyzed and processed via execution of the controller implementable steps.

In an embodiment, the device 10 comprises internal humidity and temperature sensors, 24 and 26, external (or ambient) humidity and temperature sensors, 36 and 38 and the atmospheric pressure sensor 40. In an embodiment, the foregoing device also includes heart rate sensor (45) and an internal body temperature sensor (45).

In an embodiment, the controller 28 and the user interface 30 are integrated in a single piece. In an embodiment, controller 28 is remote and in wireless communication with user interface 30. In an embodiment, controller 28 is in a wire communication with the one or more sensors provided herein. In an embodiment, controller 28 is in wireless communication with the one or more sensors provided herein. In an embodiment, the controller 28 comprises a plurality of independent sub-controllers, with one or more of the sub-controller being in wireless or wire operative communication with one or more of the sensors. One or more of the sub-controllers being in wireless or wire communication with a main controller unit of the controller 28. In an embodiment, the controller 28 includes a remote main controller unit and microcontroller in wire communication with the internal chamber sensors. In an embodiment, this microcontroller is in wire communication with the external sensors positioned on a physical surface of the device 10. In an embodiment, the microcontroller and the sensors are structurally integrated. In an embodiment, the microcontroller receives captured measurements form the sensors and transmits these measurements to the main controller unit. The main controller unit performs the assessment/analysis of the measurements to determine hyperhidrosis, types thereof, levels thereof.

In an embodiment, the assessment and analysis controller implementable steps comprise equations provided herein and stored within the memory 34 of the controller 28.

Turning now to FIGS. 2 to 6, there is shown a device 50 for capturing, collecting, and measuring a sweat sample on a skin surface of a subject in accordance with a non-limiting illustrative embodiment of the present disclosure. In this this non-restrictive illustrative embodiment, the device 50 comprises a sweat capturing and collecting body 52 and a sweat measuring and assessment arrangement, generally denoted 54.

The sweat capturing and collecting body 52 defines an outer surface 56 and an inner surface 58 and forming an inner cavity 60. The body 52 has a bell-like or dome-like shape but of course, suitable cavity forming configurations can also be contemplated within the scope of the present disclosure. The body 52 defines a pair of opposite ends 62 and 64. End 62 defines an opening 66 leading to the cavity 60. The opening 66 is circumscribed by a contact surface 68 engaging a skin surface shown in FIGS. 3, 4 and 5. The contact surface 68 in this non-limiting example is provided by a flange structure 69. End 64 defines an opening also 70 leading into the cavity 60 and through which at least a portion of the sweat measuring and assessment arrangement 54 is positioned.

Figure 3:
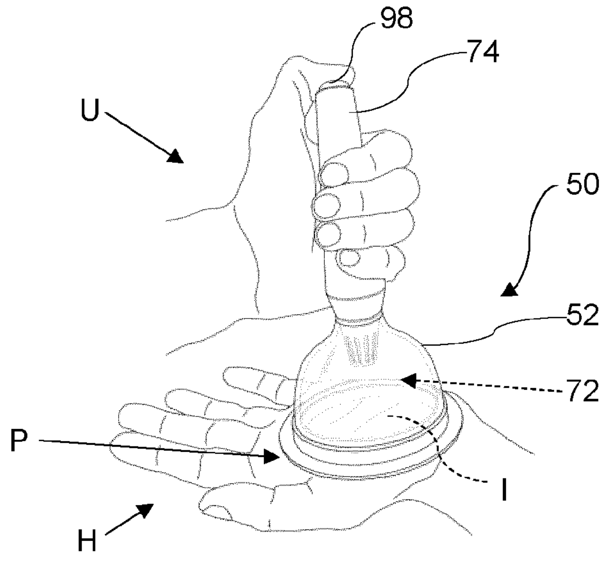
FIG. 3 is a perspective view of the device of FIG. 2 being applied to a hand skin surface of a subject in accordance with a non-limiting illustrative embodiment of the present disclosure.
Figure 4:
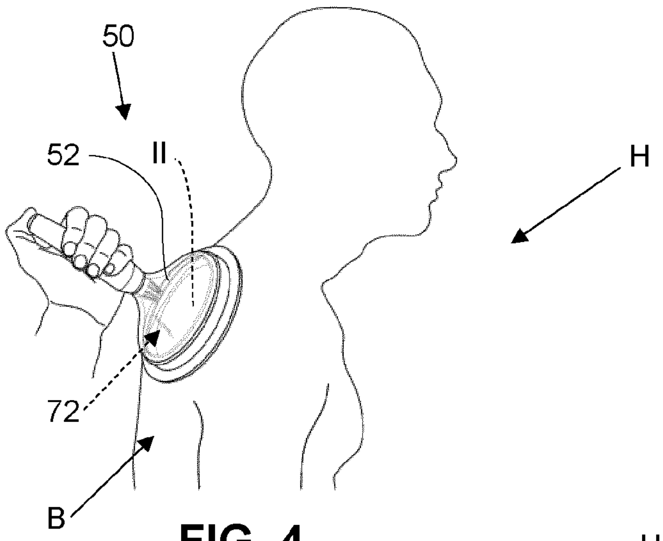
FIG. 4 is a perspective view of the device of FIG. 2 being applied to a back skin surface of a subject in accordance with a non-limiting illustrative embodiment of the present disclosure.
Figure 5:
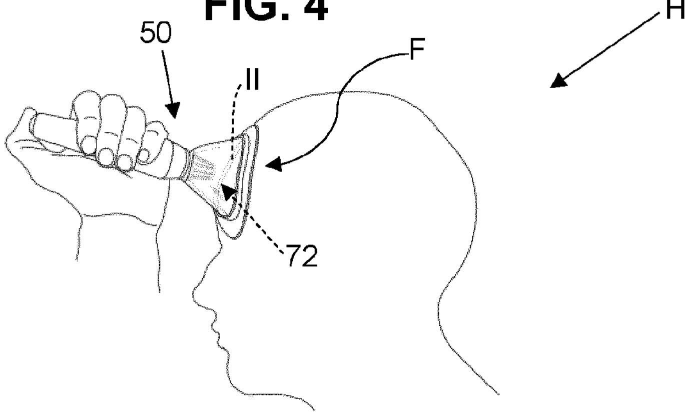
FIG. 5 is a perspective view of the device of FIG. 2 being applied to a forehead skin surface of a subject in accordance with a non-limiting illustrative embodiment of the present disclosure.

Turning now to FIGS. 3, 4 and 5, when the contact surface 68 engages a skin surface portion of a subject H such as skin surface portion I on the palm P, or skin surface portion II on the back B, or skin surface portion III on the forehead F of the subject H. The contact surface 58 provides with the skin portion I, II or III for sealing the cavity 68 thereby forming a chamber 72. Sweat is captured and collected within this hermetic chamber 72 to be measured by the sweat measuring arrangement and assessment 54 of device 50.

In this non-restrictive illustrative embodiment, the sweat measuring arrangement 54 comprises an external elongated handle 74 having a neck portion 76 for being hermetically fitted through the opening 70. A head portion or head cap 78 is connected to the neck portion 76 and is positioned within the cavity 68 and thus positioned within the chamber 72 during skin surface contact as explained above. The handle 74 provides for users (e.g. clinicians, technicians, health care providers, physicians etc.) to grip the device 50 as shown in FIGS. 3, 4 and 5 and to push the flange 69 on the skin surfaces I, II, III in order to seal the contact surface 68 therewith forming the chamber 72.

Figure 2:
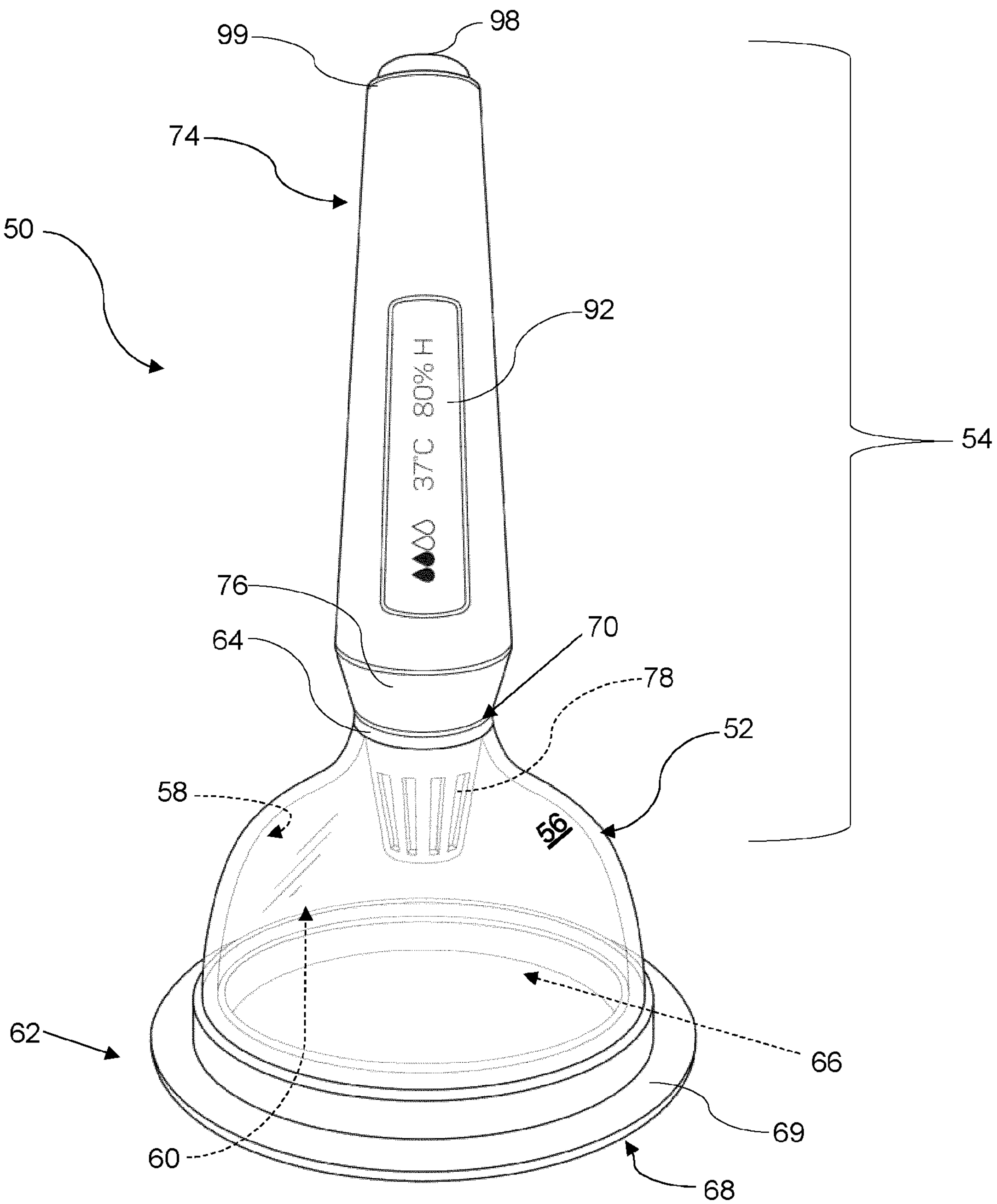
FIG. 2 is front, perspective view of a device for capturing, collecting and measuring a sweat sample on a skin surface of a subject in accordance with a non-limiting illustrative embodiment of the present disclosure.
Figure 6:
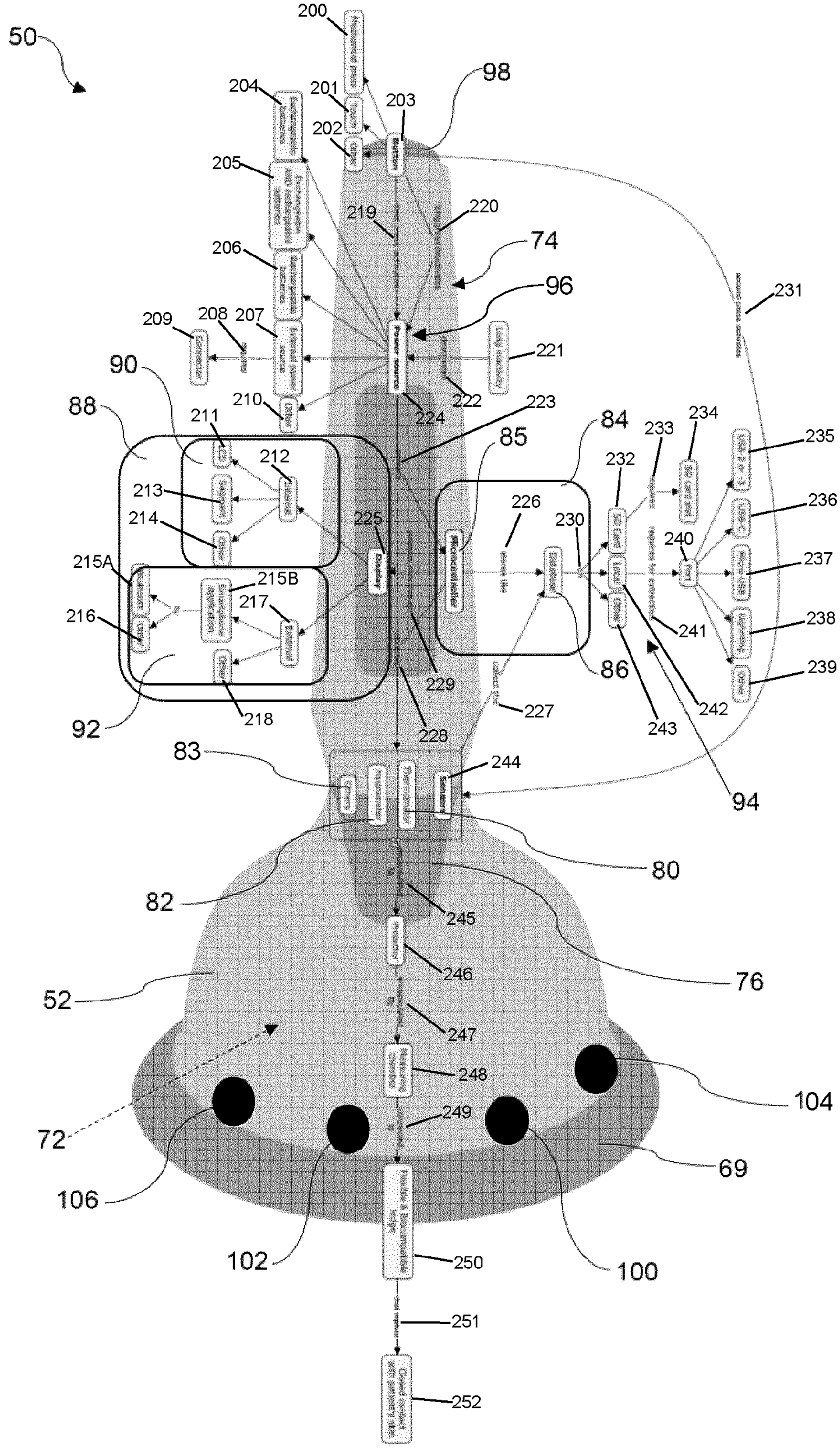
FIG. 6 is a schematic representation of the device of FIG. 1 and components thereof in accordance with a non-limiting illustrative embodiment of the present disclosure.

With reference to FIGS. 2 and 6, the components of the sweat measuring arrangement 54 will be described in accordance with a non-restrictive illustrative embodiment of the present disclosure. The sweat measuring arrangement 54 comprises a temperature sensor 80 (e.g. a thermometer) and a humidity sensor 82 (e.g. a hygrometer) positioned within the cavity 68 and thus positioned within the chamber 72 during skin surface contact. The head portion 78 houses the sensors 80 and 82 and thus acts as a protector. One or more additional sensors 83 can also be positioned within the head portion 78. The sensors 80, 82 and 83 are in operative communication with a controller 84.

In an embodiment, controller 84 comprises a microprocessor or microcontroller 85 and an associated memory or database 86. In this example, the controller 84 is positioned within the handle 74 which acts as a housing therefore. The controller 84 receives measurements from the sensors 80 and 82 which are communicated to users via a user interface 88. In an embodiment, the user interface 88 includes an integrated visual display 90. In another embodiment, the user interface 88 includes a remote device or application 92. In an embodiment, the device 50 is in operative communication (by way of its internal controller 84) to a wireless system such as Bluetooth for example, or by way of another system to an application which collects the multiple measurements. As such, the interface 88 is a remote application 92 on a remote device rather than a display 90. Indeed, the display 90 can show measurements such as temperature and humidity within the chamber and the analysis can be executed by the controller implementable steps in the remote device which then forms part of the controller as was also discussed for device 10.

In an embodiment, the measurements received by the controller 84 can be stored within the database 86 or another data storage medium 94.

The device 50 is powered by a power source 96 including batteries, external power sources etc.

The user interface 88 includes an input interface 98 such as a push button for operating the sensors provided herein to measure the sweat sample within the chamber. Indeed, the push button 98 can be provided at the free end 99 of the handle 74 allowing the user U to use their thumb for pressing the button 98 as they grip the handle 74 as shown in FIGS. 3, 4 and 5 pushing the flange 69 against the skin surface to provide a sealed chamber 72.

The bell-shaped body 52 and its flange or ledge 69 are made of flexible and resilient material allowing the body to be deformable and sufficiently pressed against the skin surface. In an embodiment, the body 52 is a treated, biocompatible semi-flexible (or semi-compliant) plastic. In an embodiment, this plastic material is treated to be resistant to condensation. In an embodiment the flange or ledge 69 is more flexible as it is in direct contract with a skin and is also made of a biocompatible plastic.

In an embodiment, body 52 is used once. In an embodiment, body 52 is reusable. The device 50 may include a plurality of bodies 52 (for one time usage or reusable or a various combinations of both) for being mounted to the handle 74 comprising different shapes, sizes and configurations adapted to different age ranges and/or and/or body shapes and/or body sizes and/or different skin surface regions. Alternatively, a universal body 52 can also be used for all ages and/or all regions.

In an embodiment, handle 74 is made of a disenfectable plastic.

In an embodiment, the contact surface 68 includes suctions for better adhesion to the skins surface.

In an embodiment, the body 52 defines microfluidic channels.

In an embodiment, the device 50 comprises ambient temperature and humidity sensors 100 and 102, respectively in order to measure the ambient temperature and humidity and to transmit this information to the controller 84 via operative communication (wire or wireless). In an embodiment, sensors 100 and 102 are positioned on the external surface 56 of the chamber forming body 52. Indeed, sensors 100 and/102 can also be positioned within the cavity 60 on along the inner surface 58. Thus, the ambient temperature humidity are measured when the dome-shaped body 52 is not engaging the skin forming the chamber therewith as provided herein but rather exposing the cavity 60 and the inner surface 58 to the ambient environment of the skin.

In an embodiment, the device 50 comprises an atmospheric pressure sensor 104 in order to measure the atmospheric pressure to transmit this information to the controller 84 via operative communication (wire or wireless). In an embodiment, sensor 104 is positioned on the external surface 56 of the chamber forming body 52. In an embodiment, sensor 104 is positioned on the internal surface 56 or positioned within the cavity 60 to read the atmospheric pressure prior to the formation of the chamber with the skin as provided herein.

The controller 84 provides, by way of the controller implementable steps, for analyzing the gradient between external and internal humidity and temperature in consideration of atmospheric pressure.

In an embodiment, other ambient sensors 106 can also be used to provide additional ambient information. Such sensors 106 can be mounted to the surfaces 56, 58, positioned within the cavity 60, positioned outside the cavity 60 or simply be in communication with the device 10 by way of the controller 84. Additional measurements to be captured include the heart rate of the subject H as well as the internal body temperature of the subject H as will be discussed further below. The following measurements provide the controller 84 with data necessary to diagnose via execution of the controller implementable steps hyperhidrosis including the type thereof and the severity level thereof.

One or more internal sensors 83 can also be positioned within the chamber 72 and positioned within the head section 76 or along the inner body surface 58. In an embodiment, sensor 83 comprises a pH sensor to provide for diagnosis (or used n the diagnosis) of the type of hyperhidrosis and its severity via the controller implementable steps as provided herein. In an embodiment, sensor 83 comprises a colorimetry sensor which provides for diagnosing (or to be used in the diagnosis of) a change of colour in the sweat such as in the case of chromhidrosis disease via the controller implementable steps as provided herein. In an embodiment, sensor 83 provides for measuring hydrostatic pressure. In an embodiment, sensor 83 comprises a conductivity sensor to measure the resistance of the patient's skin in order to diagnose (or be used in the diagnosis of) the type of hyperhidrosis, its severity or any other related diseases via the controller implementable steps as provided herein. In an embodiment, sensor 83 comprises a resistance measuring sensor which is in positioned in physical contact with the skin surface. In an embodiment, sensor 83 comprises a force measuring sensor which is positioned in physical contact with the skin surface. In an embodiment, the foregoing sensor 83 is positioned within the chamber 72. In an embodiment, the foregoing sensor is positioned outside the chamber 72.

FIG. 6 shows an schematic representation of the disclosed device including its mechanical and electronic layout. Various elements, components and interrelationships thereof are represented by a referenced box diagram. The list below provides a correspondence between each of the references 200-252 and the element they represent which is given here by way of example only:

| Reference | Element |
|---|---|
| 200 | Mechanical press |
| 201 | Touch |
| 202 | Other |
| 203 | Button |
| 204 | Exchangeable batteries |
| 205 | Exchangeable and rechargeable batteries |
| 206 | Rechargeable batteries |
| 207 | External power source |
| 208 | Requires |
| 209 | Connector |
| 210 | Other |
| 211 | LCD |
| 212 | Internal |
| 213 | Segment |
| 214 | Other |
| 215A | Bluetooth |
| 215B | Smartphone application |
| 216 | Other |
| 217 | External |
| 218 | Other |
| 219 | First press activates |
| 220 | Long press deactivates |
| 221 | Long inactivity |
| 222 | Deactivates |
| 223 | Powers |
| 224 | Power source |
| 225 | Display |
| 226 | Stores the |
| 227 | Collect the |
| 228 | Controls |
| 229 | Press data through |
| 230 | By |
| 231 | Second press activates |
| 232 | SD card |
| 233 | Requires |
| 234 | SD card slot |
| 235 | USB -2 or -3 |
| 236 | USB -C |
| 237 | Micro-USB |
| 238 | Lighting |
| 239 | Other |
| 240 | Port |
| 241 | Requires for extraction |
| 242 | Local |
| 243 | Other |
| 244 | Sensors |
| 245 | Encapsulated by |
| 246 | Protector |
| 247 | Encapsulated by |
| 248 | Mechanical chamber |
| 249 | Connected to |
| 250 | Flexible biocompatible ledge |
| 251 | That makes |
| 252 | Closed contact with patient's skin |

In an embodiment, a data table is stored within the memory of the controller 84 in order to comparatively diagnose hyperhidrosis and its severity on the basis of the measurements captured by device 10 via the controller implementable steps as provided herein.

In an embodiment, measurements associated with percentages of the population are obtained in order to disclose a percentile of the population and to produce a diagnosis for hyperhidrosis and its severity.

In an embodiment, the devices, controller implementable steps and methods herein provide for determining the efficacy of antiperspirant treatments. In an embodiment, the devices, controller implementable steps and methods herein provide for determining the efficacy of botulinum toxin treatments. In an embodiment, the devices, controller implementable steps and methods herein provide for determining the efficacy of surgeries to treat a hyperhidrosis condition such as a sympathectomy surgery. In an embodiment, the devices, controller implementable steps and methods herein provide for determining the efficacy of iontophoresis treatments for hyperhidrosis. In an embodiment, the devices, controller implementable steps and methods herein provide for determining the efficacy of other treatments for hyperhidrosis such as drugs and other mechanisms.

In an embodiment, the devices, controller implementable steps and methods herein provide measuring the sweat's ionic composition which is useful for a psychological assessment of subject, including stress and anxiety evaluations, amongst other possible conditions. The foregoing is useful for law enforcement officers or equivalents to aid in lie detection processes during investigations.

In an embodiment, the controller implementable steps and methods herein provide measurement acquisition on a regular interval (see Table II below) over a specified period of time lapse (see Table I below) and execute calculations via equations stored in the memory of the controller 84 to associate an output sweat secretion rate and a temperature measurement to a type and a severity of hyperhidrosis.

Tables I and II below show time evaluation intervals and time sampling rates. Table I shows non-limiting examples of measurement acquisition intervals. Non-restrictive but more frequently used intervals are highlighted in bold.

TABLE I

| Evaluation time bounds | |
|---|---|
| Start of evaluation (s) | End of evaluation (s) |
| 0 s | 5 s |
| 0 s | 10 s |
| 0 s | 20 s |
| **0 s** | **30 s** |
| 0 s | 45 s |
| 0 s | 1 min |
| 0 s | 2 min |
| 0 s | 3 min |
| 0 s | 4 min |
| 0 s | 5 min |
| 0 s | 10 min |
| 1 s | 5 s |
| 1 s | 10 s |
| 1 s | 20 s |
| 1 s | 30 s |
| 1 s | 45 s |
| **1 s** | **1 min** |
| 1 s | 2 min |
| 1 s | 3 min |
| 1 s | 4 min |
| 1 s | 5 min |
| 1 s | 10 min |
| 2 s | 10 s |
| 2 s | 20 s |
| 2 s | 30 s |
| 2 s | 45 s |
| 2 s | 1 min |
| 2 s | 2 min |
| 2 s | 3 min |
| 2 s | 4 min |
| 2 s | 5 min |

TABLE I-continued

| Evaluation time bounds | |
|---|---|
| Start of evaluation (s) | End of evaluation (s) |
| 2 s | 10 min |
| 3 s | 10 s |
| 3 s | 20 s |
| 3 s | 30 s |
| 3 s | 45 s |
| 3 s | 1 min |
| 3 s | 2 min |
| 3 s | 3 min |
| 3 s | 4 min |
| 3 s | 5 min |
| 3 s | 10 min |
| 4 s | 10 s |
| 4 s | 20 s |
| 4 s | 30 s |
| 4 s | 45 s |
| 4 s | 1 min |
| 4 s | 2 min |
| 4 s | 3 min |
| 4 s | 4 min |
| 4 s | 5 min |
| 4 s | 10 min |
| 5 s | 10 s |
| 5 s | 20 s |
| 5 s | 30 s |
| 5 s | 45 s |
| 5 s | 1 min |
| 5 s | 2 min |
| 5 s | 3 min |
| 5 s | 4 min |
| 5 s | 5 min |
| 5 s | 10 min |

Table II below shows a list of non-limiting sampling rates and associated sampling periods of evaluations. Non-restrictive but more frequently used sampling rate/sampling periods are highlighted in bold.

TABLE II

| Sampling rate (sample/second) | Sampling period (second) |
|---|---|
| 0.01 | 100 (1 min 40 sec) |
| 0.05 | 20 |
| 0.1 | 10 |
| 0.5 | 2 |
| 1 | 1 |
| **2** | **0.5** |
| 3 | 0.33 |
| 4 | 0.25 |

In an embodiment, the devices and methods herein are used on patients diagnosed with primary, secondary or focal hyperhidrosis or on patients exhibiting symptoms relative to these conditions entailing a suspicion of diagnosis of one of these conditions from the healthcare provider (i.e. user). In an embodiment, the devices and methods are used in a controlled environment with adjustable parameters as provided herein.

In an embodiment, the devices and methods herein provide for measuring internal humidity of the chamber formed on the skin surface of the subject as well as the ambient humidity and temperature (external to this chamber) but proximal the skin surface as well as the atmospheric pressure. Indeed, the devices and methods herein provide for determining a temperature gradient and a humidity gradient in order to assess the impact of the environmental conditions on the sweat rate of the subject thereby providing for diagnosing hyperhidrosis as well as the severity thereof. In fact, the body's perspiration is highly influenced by the external environment as it is a physiological reaction that allows constant thermoregulation of the body in response to external stimuli. Therefore, the devices and methods of the disclosure take into account the values of the following parameters: the temperature gradient (internal vs. external of the chamber), the humidity gradient (internal vs. external of the chamber) and the atmospheric pressure. Individuals are usually more prone to sweat in a humid environment than in a dry environment and thus the devices and methods herein take the external conditions into account in order to standardize the measurement results regardless of the ambient environment of the subject. The foregoing provides for focusing on the aspect of an individual's perspiration that is caused by hyperhidrosis rather than the aspect caused by the ambient environmental conditions that a subject finds themself in.

In an embodiment, the controller implementable steps provide for the use of a theoretical control (described further below) to which all the sweat samples are compared to.

In an embodiment, there is provided a correlation between the heart rate and sweat rate of the subject. In fact, heart rates with values far from the established steady state interval are indicative of a certain physical imbalance and are often associated with physiological responses such as sweating.

In an embodiment, the internal temperature of the body is also collected. In fact, the internal temperature in the collecting chamber is different from the temperature inside the body. The internal temperature in the chamber represents the temperature at the surface of the skin which is directly related to the evaporation of sweat. On the other hand, the internal temperature of the body corresponds to the general health state of the subject which is useful for determining whether the subject's sweat is due to hyperhidrosis or another underlying issue.

In an embodiment, atmospheric pressure is a modulating parameter of sweat production. In fact, in higher altitudes the atmospheric pressure decreases which increases sweating of the subject. Accordingly, atmospheric pressure is also considered.

The present disclosure provides for linking various parameters (such as the relative humidity, the specific humidity, the molar masses of water and air and the molar fraction of water in air) based on the laws of thermodynamics.

In an embodiment, temperature, humidity and pressure are measured and processed to provide two results for determining a hyperhidrosis level of a subject: the specific humidity gradient and the molecular concentration gradient of water in the air. These two values are strongly correlated with the hyperhidrosis severity of the subject since the more the subject sweats in a given time lapse, the greater specific humidity and molecular concentration gradients are. In fact, when an individual sweats, the sweat is produced in a liquid form on the surface of the skin which then evaporates in the chamber until condensation around the sensors within the chamber. Thus, for a standard timestamp, if the subject sweats considerably, an important change in molecular concentration and in specific humidity will be noted since an important quantity of water will be in the air contained within the collecting chamber.

In an embodiment, the temperature and humidity gradients provided herein are not related to the specific humidity and to the molecular concentration by a linear relation. Therefore, analysis of the measurements provided herein involve modulating (i.e. augmenting/attenuation) factors conferring more or less weight to each parameter in the calculation of the specific humidity gradient and the molecular mass gradient.

In an embodiment, the parameters required for measuring a sweat sample in order to determine or be used in determining hyperhidrosis and the severity (or level thereof) are as follows:

$RH_{int}$: Internal relative humidity of the collecting chamber (%).

$RH_{ext}$: External relative humidity of the collecting chamber (%).

$T_{int}$: Internal temperature of the collecting chamber (° C.).

$T_{ext}$: External temperature of the collecting chamber (° C.).

P: Atmospheric pressure (kPa).

t: time(s).

The foregoing parameters are captured and processed via the controller implementable steps as provided herein.

In an embodiment, establishing the hyperhidrosis severity level of a subject is based on multiple variables: the relative humidity, the internal temperature of the collecting chamber, the external temperature outside of the chamber, the atmospheric pressure and the elapsed time.

In an embodiment, the controller implementable steps execute the following functions to obtain the two parameters presented below:

$$f_1(RH_{int_t}, RH_{ext_t} P_t, T_{int_t}, T_{ext_t}) = C(t)$$

$$f_2(RH_{int_t}, RH_{ext_t}, P_t, T_{int_t}, T_{ext_t}) = q(t)$$

These above functions provide for calculating molecular water concentration C within the collecting chamber at timestamp (t) i.e. C (t) and specific humidity q within the collecting chamber at timestamp (t) i.e. q (t). The molecular water concentration C is the amount of substance per unit volume of solution, and the specific humidity q is the mass of water vapor per unit mass of moist air.

These functions are calculated at two different time stamps, namely at the beginning of the treatment (t=i) and at the end of the treatment (t=f); and for each time, in two different environments: internal (inside the chamber) represented by int and external (outside the chamber) represented by ext.

A control group such as a matrix of witness values is used to quantify the influence of the environment on the perspiration and by extension, on the parameters C (t) and q (t). By definition, a witness or control is any individual who does not suffer from hyperhidrosis and whose sweat excretion rate is solely affected by the environmental conditions they are in. The purpose of using a witness is to isolate the effect of the environment on the patient's hyperhidrosis level. To reach that goal, a specific combination of temperature and relative humidity is chosen and defined as control parameters for which values of molecular concentration and specific humidity are calculated as was mentioned before. These values are constant theoretical values. These parameters are calculated at the beginning and end of the evaluation performed in pre-defined environmental conditions (room temperature, duration of evaluation, etc.). Hence, for each specific witness combination of temperature and relative humidity, the initial and final internal concentrations are calculated. The associated gradient of concentration is then calculated for that specific combination, hence composing the witness population to build a first witness table. A group of witness subjects is associated to each parameter combination and the value entered in the table for each combination corresponds to the mean C deducted from the results of the group members. This table contains values of gradients of molecular concentration of water in the air contained inside the chamber in function of diverse temperature-relative humidity combinations. Each temperature-relative humidity combination is also associated to a value of specific humidity that is measured at the beginning and end of the treatment as well in order to calculate the specific humidity gradient which is reported in a second witness table. The next step is to realize the same operations on a patient suffering from hyperhidrosis or showing symptoms related to this pathology. The experimental conditions, temperature and relative humidity, in which the hyperhidrosis patient is being tested are noted and are used to determine which witness is associated to the current experimental environment. Once the concordant witness values associated to the same temperature and relative humidity parameters are identified, the witness values can be compared and mathematically manipulated based on the parameters associated to the hyperhidrosis patient's values. However, it should be noted that this simple comparison and mathematical manipulation between hyperhidrosis patient results and witness patient results can only be accurate if both are tested in the exact same environmental conditions since the tables represent C and q based on the initial values of T and RH inside the measuring chamber. In order to reach a comparison ground between subject and witness no matter their experimental conditions, a general modulating factor noted as $f_{env}$, is added in the algorithm to represent the effect of the environment on the values of C and q of the subjects. For example, for a room temperature of T=22.5° C. and a room relative humidity RH=35%, for a hyperhidrosis patient, a gradient of concentration between the initial and final time is calculated. Then, for a witness population, for a temperature T=24° C. and a relative humidity RH=50%, a gradient of concentration between the final and initial time is calculated. This last gradient and the first one are mathematically manipulated to obtain the water concentration only due to hyperhidrosis and its severity level. This mathematical manipulation is then compared to a table which associates each level of severity to a range of concentration gradients. The same is performed for specific humidity. Moreover, for a hyperhidrosis patient in a room at T=24° C. and RH=50%, the comparison between witness patient and hyperhidrosis patient will include the use of a modulating factor to consider the difference between both experimental environments. The modulating factor will contribute to attenuate or to inflate the concentration gradient or the specific humidity gradient depending on the environment and its effect on the patient's sweat excretion rate. The environmental factor $f_{env,C}$ corresponds to the influence of the environmental conditions on the molecular concentration of water in the internal air of the chamber and its influence can be determined according to Table 1 below. Table 1 associates values of $f_{env,C}$ to ranges of differences between the witness patients' environmental conditions and the hyperhidrosis patient's environmental conditions.

TABLE 1

Environmental factor deducted from the effect of the environment on the molecular concentration values

| Difference in environmental conditions | Environmental factor for concentration values ($f_{env, C}$) |
|---|---|
| $[dc_1, dc_2]$ | $f_{env, C, 1}$ |
| $[dc_3, dc_4]$ | $f_{env, C, 2}$ |
| $[dc_5, dc_6]$ | $f_{env, C, 3}$ |
| $[dc_7, dc_8]$ | $f_{env, C, 4}$ |
| . . . | . . . |

The internal gradients between the two parameters (molecular water concentration and specific humidity) and the modulating factors associated to the external parameters (temperature, relative humidity, pressure) are determined, compared and manipulated mathematically with the correspondent witness values to assess the influence of hyperhidrosis on the sweat rate of the subject between the initial and final time.

The following equations are stored in the memory of the system controller and performed thereby via computer-implementable steps:

$$\Delta C_{witness} = C_{f_{int_w}} \quad C_{i_{int_w}}$$

$$\Delta C_{witness} = C_{f_{int_w}}\left(RH_{f_{int}}; T_{f_{int}}\right) \quad C_{i_{int_w}}\left(RH_{i_{int}}; T_{i_{int}}\right)$$

$$\Delta C_{patient} = C_{f_{int_p}} \quad C_{i_{int_p}}$$

$$\Delta C_{evaluation} = (\Delta C_{patient} \quad \Delta C_{witness}) \quad f_{env,C}$$

Wherein $$C_{i_{int_w}}$$

represents the average internal molecular water concentration at the initial time from a sample of witnesses.

Wherein $$C_{f_{int_w}}$$

represents the average internal molecular water concentration at the final time from a sample of witnesses.

Wherein $\Delta C_{witness}$ represents the internal molecular water concentration gradient from the average internal molecular water concentrations from a sample of witnesses at the initial and final times.

Wherein $$C_{i_{int_p}}$$

represents the internal molecular water concentration at the initial time for a subject (i.e. a patient)

Wherein $$C_{f_{int_p}}$$

represents the internal molecular water concentration at the final time for a patient Wherein $\Delta C_{patient}$ represents the internal molecular water concentration gradient from the internal molecular water concentrations at the initial and final times.

Wherein $\Delta C_{evaluation}$ represents the concentration gradient used to be compared to the severity scale in order to determine a hyperhidrosis severity level.

The same method is applied for the specific humidity and a matrix of associated values for a witness population is used. The environmental factor $f_{env,q}$ corresponds to the influence of the environmental conditions on the specific humidity in the internal air of the chamber and its influence can be determined according to Table 2 below. Table 2 associates values of $f_{env,g}$ to ranges of differences between the witness patients' environmental conditions and hyperhidrosis patient's environmental conditions.

TABLE 2

| Environmental factor deducted from the effect of the environment on specific humidity values | |
|---|---|
| Difference in environmental conditions | Environmental factor for specific humidity values ($f_{env,\ q}$) |
| $[dq_1, dq_2]$ | $f_{env,\ q,\ 1}$ |
| $[dq_3, dq_4]$ | $f_{env,\ q,\ 2}$ |
| $[dq_5, dq_6]$ | $f_{env,\ q,\ 3}$ |
| $[dq_7, db_8]$ | $f_{env,\ q,\ 4}$ |
| . . . | . . . |

The same operations apply to the specific humidity with the following equations are stored in the memory of the system controller and performed thereby via computer-implementable steps:

$$\Delta q_{witness} = q_{f\_int\_w} \quad q_{i\_int\_w}$$

$$\Delta q_{witness} = q_{fint_w}\left(RH_{fint}; T_{fint}\right) \quad q_{iint_w}\left(RH_{iint}; T_{iint}\right)$$

$$\Delta q_{patient} = q_{f\_int\_p} \quad q_{i\_int\_p}$$

$$\Delta q_{evaluation} = (\Delta q_{patient} \quad \Delta q_{witness}) \quad f_{env,q}$$

Wherein $q_{i\_int\_w}$ represents the average internal specific humidity at the initial time from a sample of witnesses.

Wherein $q_{f\_int\_w}$ represents the average internal specific humidity at the final time from a sample of witnesses.

Wherein $\Delta q_{witness}$ represents the internal specific humidity gradient from the average internal specific humidity from a sample of witnesses at the initial and final time.

Wherein $q_{i\_int\_p}$ represents the internal specific humidity at the initial time for a patient.

Wherein $q_{f\_int\_p}$ represents the internal specific humidity at the final time for a patient Wherein $\Delta q_{patient}$ represents the internal specific humidity gradient from the internal specific humidity at the initial and final time.

Wherein $\Delta q_{evaluation}$ represents the specific humidity used to be compared to the severity scale in order to determine a hyperhidrosis severity level.

The parameters above are generally expressed by the following equations (stored in the memory of the controller):

$$C_{t=}[H_2O]_t = x_{H_2O_t} \quad n_{air_t} \quad N_A \quad 10^{-6}$$

-continued $$q_t = \frac{x_{H_2O_t} \quad M_{H_2O}}{x_{H_2O_t} \quad M_{H_2O} + (1 \quad x_{H_2O_t}) \quad M_{dry}}$$

The constants used in the two precedent equations are presented below:

Molar gas constant is the constant of proportionality that relates the energy scale to the temperature scale and the scale representing the amount of substance and is provided as follows:

$$R = 8.31447215 J \ \text{mol}^{-1} K^{-1}$$

Avogadro constant is the number of elementary units in one mole of any substance and is provided as follows:

$$N_A = 6.0221415 \cdot 10^{23} \text{mol}^{-1}$$

Vapor pressure of water is the pressure at which the gas phase is in equilibrium with the liquid phase. To evaluate the vapor pressure of water, a polynomial approximation of the 6th order is used with less than a one percent error. The polynomial formulation for saturation vapor pressure is:

$$e(T) = a_0 + T \quad (a_1 + T \quad (a_2 + T \quad (a_3 + T \quad (a_4 + T \quad (a_5 + T \quad a_6)))))$$

Wherein T is temperature in degrees centigrade and the constants have the following values:

| Constant | Water | Ice |
|---|---|---|
| a0 | 6.107799961 | 6.109177956 |
| a1 | 4.436518521 · 10-1 | 5.034698970 · 10-1 |
| a2 | 1.428945805 · 10-2 | 1.886013408 · 10-2 |
| a3 | 2.650648471 · 10-4 | 4.176223716 · 10-4 |
| a4 | 3.031240396 · 10-6 | 5.824720280 · 10-6 |
| a5 | 2.034080948 · 10-8 | 4.838803174 · 10-8 |
| a6 | 6.136820929 · 10-11 | 1.838826904 · 10-10 |

$$e = \min(e_{water}, e_{ice})$$

For the temperature between −50 et 0° C.: min ($e_{water}$, $e_{ice}$)=$e_{ice}$.

For the temperature between 0 et 100° C.: min ($e_{water}$, $e_{ice}$)=$e_{water}$.

In an embodiment, the vapor pressure of water would be $e_{water}$, hence e(t)=$e_{water}$.

Air density is the mass per unit volume of Earth's atmosphere and is provided as follows:

$$n_{air} = \frac{P \quad 100}{R(T + 273.15)}$$

P is the absolute pressure of the system.

Relative humidity indicates a present state of absolute humidity relative to a maximum humidity given the same temperature and is provided as follows:

$$RH = \frac{P_{H_2O} \;\; 100}{e(T)}$$

Partial pressure of water is the pressure at which water vapor is in thermodynamic equilibrium with its condensed state and is provided as follows:

$$P_{H_2O} = \frac{RH \;\; e(T)}{100}$$

Molar fraction is the amount of a constituent (expressed in moles), $n_i$, divided by the total amount of all constituents in a mixture and is provided as follows:

$$x_{H_2O} = \frac{P_{H_2O}}{P}$$

Molar mass of water is the mass of a mole (=unity of measure of the number of particles in matter) of water and is provided as follows:

$$M_{H_2O} = 18.01534 \text{ g.mol}^{-1}$$

Molar mass of dry air is the mass of a mole of dry air and is provided as follows:

$$M_{dry} = 28.9644 \text{ g.mol}^{-1}$$

The constants presented above can all be used to determine the molecular water concentration in function of the relative humidity, the temperature and the pressure as shown in the equation below, where $[H_2O]_t$ is the molecular water concentration at a time t. Hence, the initial equation: $[H_2O]_t = X_{H_2O_t} + n_{air_t} \; N_A \; 10^{-6}$ can now be expressed as:

$$[H_2O]_t = \frac{RH_t \;\; e(T)_t}{R(T_t + 273.15)} \;\; N_A \;\; 10^{-6}$$

The parameters presented above can also all be used to determine the specific humidity in function of the relative humidity, the temperature and the pressure as shown in the equation below, where $q_t$ is the specific humidity at a time t. Hence, the initial equation:

$$q = \frac{x_{H_2O} \;\; M_{H_2O}}{x_{H_2O} \;\; M_{H_2O} + (1 - x_{H_2O}) \;\; M_{dry}}$$

can now be expressed as:

$$q_t = \frac{\frac{RH_t \;\; e(T)_t}{100 \;\; P_t} M_{H_2O}}{\frac{RH_t \;\; e(T)_t}{100 \;\; P_t} M_{H_2O} + \left(1 \;\; \frac{RH_t \;\; e(T)_t}{100 \;\; P_t}\right) M_{dry}}$$

Given the variables t=i (initial time) and t=f (final time) and the associated external and internal parameters for the temperature ($T_{ext}$, $T_{int}$), absolute pressure at time t (Pt) and relative humidity ($RH_{ext}$, $RH_{int}$), the following gradients are calculated:

$$\Delta C = C_f \;\; C_i$$

$$\Delta C_{mol} = [H_2O]_f \;\; [H_2O]_i$$

$$\Delta C_{mol} = ([H_2O]_{int_f} \;\; [H_2O]_{int_i}) + ([H_2O]_{ext_i} \;\; [H_2O]_W) \;\; ([H_2O]_{ext_f} \;\; [H_2O]_W)$$

$$\Delta q = q_f \;\; q_i$$

$$\Delta q = (q_{int_f} \;\; q_{int_i}) \;\; (q_{ext_f} \;\; q_W) + (q_{ext_i} \;\; q_W)$$

The foregoing equations are stored in the memory of the controller and calculated on the basis of the measurements received as provided herein.

In another embodiment, an alternate way to determine the specific humidity is through the mass concentration as provided below:

Mass concentration of water is the mass of water per unit volume of the solution and is provided as follows:

$$c_m = x_{H_2O} \;\; n_{air} \;\; M_{H_2O}$$

$$\frac{c_m}{n_{air}} = x_{H_2O} \;\; M_{H_2O}$$

Hence, when considering the above with the previous equation:

$$q_t = \frac{x_{H_2O} \;\; M_{H_2O}}{x_{H_2O} \;\; M_{H_2O} + (1 - x_{H_2O}) \;\; M_{dry}}$$

the specific humidity can be expressed as follows:

$$q_t = \frac{\frac{c_m}{n_{air}}}{\frac{c_m}{n_{air}} + \left(1 \;\; \frac{RH_t \;\; e(T)_t}{100 \;\; P_t}\right) M_{dry}}$$

In another embodiment, an alternate way to determine the specific humidity is through the molecular concentration as shown in the following equations:

$$[H_2O]_t = x_{H_2O_t} \; n_{air_t} \; N_A \; 10^{-6}$$

$$x_{H_2O_t} = \frac{[H_2O]_t}{n_{air_t} \; N_A \; 10^{-6}}$$

Hence, when considering the above with the previous equation:

$$q_t = \frac{x_{H_2O} \; M_{H_2O}}{x_{H_2O} \; M_{H_2O} + (1 - x_{H_2O}) \; M_{dry}}$$

the specific humidity can be expressed as follows:

$$q_t = \frac{\frac{[H_2O]_t}{n_{air_t} \; N_A \; 10^{-6}} M_{H_2O}}{\frac{[H_2O]_t}{n_{air_t} \; N_A \; 10^{-6}} \; M_{H_2O} + \left(1 \quad \frac{[H_2O]_t}{n_{air_t} \; N_A \; 10^{-6}}\right) \; M_{dry}}$$

The foregoing equations are stored in the memory of the controller and calculated on the basis of the measurements received as provided herein.

In an embodiment, the controller implementable steps and methods herein also take into consideration two additional parameters, namely the heart rate (HR) of the subject and the internal body temperature (BT) of the subject as well as a modulating factor for each of the foregoing ($f_{HR}$: heart rate factor and $f_{BT}$: body temperature factor). For each of these two parameters (heart rate and internal body temperature), the user refers to a correspondence table in order to determine the value of the associated factor. A given value of a parameter (HR, BT) corresponds to a given factor ($f_{HR}$, $f_{BT}$). The correspondence table is stored in the memory of the controller and the calculated parameters are compared thereto via the controller implementable steps.

The heart rate factor $f_{HR}$ corresponds to the influence of the heart rate on the perspiration of the subject and as such on hyperhidrosis severity analysis, and its influence can be determined according to Table 3 below. The internal body temperature factor $f_{BT}$ corresponds to the influence of the internal body temperature on the perspiration of the subject and as such on hyperhidrosis severity analysis and its influence can be determined according to Table 4 below. Therefore, the equations which take the heart rate and internal body temperature into consideration in order to provide for calculating the molecular concentration of water and the specific humidity are stored in the memory of the controller and are as follows:

Molecular Water Concentration:

$$[H_2O]_t = \frac{RH_t \; e(T)_t \; f_{HR} \; f_{BT}}{R(T_t + 273{,}15)} \; N_A \; 10^{-6}$$

Specific Humidity:

$$q_t = \frac{\frac{RH_t \; e(T)_t}{100 \; P_t} M_{H_2O} \; f_{HR} \; f_{BT}}{\frac{RH_t \; e(T)_t}{100 \; P_t} M_{H_2O} + \left(1 \quad \frac{RH_t \; e(T)_t}{100 \; P_t}\right) M_{dry}}$$

Specific Humidity Expressed with the Mass Concentration:

$$q_t = \frac{\frac{c_m}{n_{air}} \; f_{HR} \; f_{BT}}{\frac{c_m}{n_{air}} + \left(1 \quad \frac{RH_t \; e(T)_t}{100 \; P_t}\right) \; M_{dry}}$$

Specific Humidity Expressed with the Molecular Concentration:

$$q_t = \frac{\frac{[H_2O]_t}{n_{air} \; N_A \; 10^{-6}} \; M_{H_2O} \; f_{HR} \; f_{BT}}{\frac{[H_2O]_t}{n_{air} \; N_A \; 10^{-6}} \; M_{H_2O} + \left(1 \quad \frac{[H_2O]_t}{n_{air} \; N_A \; 10^{-6}}\right) \; M_{dry}}$$

TABLE 3

| Heart rate factor values associated to the measured heart rate of the patient | |
|---|---|
| Heart rate (r) | Heart rate factor ($f_{HR}$) |
| $[r_1, r_2]$ | $f_{HR, 1}$ |
| $[r_3, r_4]$ | $f_{HR, 2}$ |
| $[r_5, r_6]$ | $f_{HR, 3}$ |
| $[r_7, r_8]$ | $f_{HR, 4}$ |
| . . . | . . . |

TABLE 4

| Body temperature factor values associated to the measured body temperature of the patient | |
|---|---|
| Body temperature (b) | Body temperature factor ($f_{BT}$) |
| $[b_1, b_2]$ | $f_{BT, 1}$ |
| $[b_3, b_4]$ | $f_{BT, 2}$ |
| $[b_5, b_6]$ | $f_{BT, 3}$ |
| $[b_7, b_8]$ | $f_{BT, 4}$ |
| . . . | . . . |

Table 5 below is used to match the corresponding ranges of specific humidity ($q_{evaluation}$) and molecular concentration ($C_{evaluation}$) to a hyperhidrosis severity level. Therefore, the controller implementable steps and the methods herein provide for calculating the gradient of specific humidity and the molecular water concentration and determine the severity of hyperhidrosis if both of them are in the correct ranges of Table 5 Hence, if $\Delta q$ belongs to $[x_1, x_2]$ and $C_{evaluation}$ belongs to $[y_1, y_2]$, the severity level of hyperhidrosis would be 0. The other severity levels 1, 2, 3 and 4 are determined with respectively $[x_3, x_4]$, $[x_5, x_6]$, $[x_7, x_8]$, $[x_9, x_{10}]$; and with $[y_3, y_4]$, $[y_5, y_6]$, $[y_7, y_8]$ and $[y_9, y_{10}]$.

TABLE 5

| Hyperhidrosis severity level diagnosis | | |
|---|---|---|
| Specific humidity $\Delta q_{evaluation}$ | Molecular concentration (molecules/cm$^3$) $C_{evaluation}$ | Hyperhidrosis severity level |
| $[x_1, x_2]$ | $[y_1, y_2]$ | 0 |
| $[x_3, x_4]$ | $[y_3, y_4]$ | 1 |

TABLE 5-continued

| Hyperhidrosis severity level diagnosis | | |
|---|---|---|
| Specific humidity $\Delta q_{evaluation}$ | Molecular concentration (molecules/cm$^3$) $C_{evaluation}$ | Hyperhidrosis severity level |
| $[x_5, x_6]$ | $[y_5, y_6]$ | 2 |
| $[x_7, x_8]$ | $[y_7, y_8]$ | 3 |
| $[x_9, x_{10}]$ | $[y_9, y_{10}]$ | 4 |

In another embodiment, the determination of the hyperhidrosis severity level can equivalently be determined through a sweat secretion rate instead of a sweat secretion quantity. The above steps are carried out during a specified period of time. However, that period can be modified if the final result is a rate instead of a quantity. Accordingly, and in an embodiment, the controller implementable steps and method provide for the determination of the hyperhidrosis severity level, independent of the time scale. The value of specific humidity rate (qr) would hence be noted as:

$$qr = \frac{\frac{RH_t\ e(T)_t}{100\ P_t} M_{H_2O}\ f_{HR}\ f_{BT}}{\left(\frac{RH_t\ e(T)_t}{100\ P_t} M_{H_2O} + \left(1\ \frac{RH_t\ e(T)}{100\ P_t}\right) M_{dry}\right)\ \Delta t}$$

wherein Δt is the time (in seconds).

In another embodiment, the determination of the hyperhidrosis severity level can be determined considering the different possibilities of volume and of surface of the collecting chamber. Therefore, the molecular water concentration is expressed as follow, wherein Vis the volume of the chamber and Sis surface of the chamber:

$$[H_2O]_t = \frac{RH_t\ e(T)_t\ f_{HR}\ f_{BT}}{R(T_t + 273{,}15)}\ N_A\ 10^{-6}\ \frac{S}{V}$$

Moreover, the specific humidity is expressed as follow, wherein Vis the volume of the chamber and Sis surface of the chamber.

$$q_t = \frac{\frac{RH_t\ e(T)_t}{100\ P_t} M_{H_2O}}{\frac{RH_t\ e(T)_t}{100\ P_t} M_{H_2O} + \left(1\ \frac{RH_t\ e(T)_t}{100\ P_t}\right) M_{dry}}\ \frac{S}{V}$$

The two other ways to express the specific humidity are expressed with the new factor $$\frac{S}{V}.$$

In an embodiment, the present disclosure provides for a device and method to evaluate the evolution of hyperhidrosis in a subject (or patient). In practice, the clinician performs a first reading (or measure) of a subject's hyperhidrosis condition at an initial time stamp. Later on (days, weeks, months) a second reading is performed at a second time stamp. Indeed, the environmental conditions at the initial and second time stamps are not identical and thus we do not have absolute readings in a vacuum but rather environmentally dependent readings making it difficult for the clinician to assess the evolution of hyperhidrosis between two or more time stamps. Accordingly, there is provided an environmental factor that is taken into account and that transposes the environmental conditions of one reading (first or second time stamp) to the environmental conditions of the other reading (first or second time stamp) in order to place the two readings (or measures) for each respective time stamp on equal footing as if they had been taken in the same environmental conditions.

In an embodiment, an auto-control measure per subject (or patient) is used to quantify the influence of the environment on the patient's perspiration and by extension, on the parameters $C_t$ and $q_t$, and therefore to quantify the evolution of their perspiration. An auto-control measure is any measure of a patient taken in a reproducible and accurate manner under considered environmental conditions to be used as a control for any of the patient's future measures. The purpose of using an auto-control measure per patient is to isolate the effect of the environment on the patient's entire perspiration level and to evaluate the evolution of their perspiration. To reach that goal, specific combinations of temperature and relative humidity are chosen and defined as control parameters for which values of molecular concentration and specific humidity are calculated as was mentioned before. These values are comparative values. These parameters are calculated at the beginning and at the end of the evaluation performed in the pre-defined environmental conditions (room temperature, duration of evaluation, etc.). Hence, for each control combination of temperature and relative humidity, the initial and final internal concentrations are calculated. The associated gradient of concentration is then calculated for each combination, hence composing the auto-control measures of the patient to build comparative values associated with the typical environments. A patient is associated with each auto-control measure associated with a parameter combination and entered in a table. This table (Table 6 below) contains values of gradients of molecular concentration of water in the air contained inside the chamber in function of diverse temperature-relative humidity combinations. Each temperature-relative humidity combination is also associated with a value of specific humidity that is measured at the beginning and at the end of the treatment as well in order to calculate the specific humidity gradient which is reported in a second auto-control table.

The next step is to perform the same operations during the next evaluation of the same patient and to evaluate the evolution of their perspiration despite other environmental combinations in order to evaluate the evolution of their hyperhidrotic severity level. To reach that goal, the newly taken values are compared and mathematically manipulated based on the parameters associated to the comparative values of the same patient. In order to assess the evolution of a patient's perspiration level over time, no matter the experimental (i.e. environmental) conditions, a general modulating factor noted as Fenv, is added in the algorithms provided herein (see further below) to represent the effect of the environment on the values of the subjects/patients. The different concentration gradients of the comparative values are mathematically manipulated to obtain Fenv. For example, for a room temperature of T=22.5° C. and a room relative humidity RH=35%, for a hyperhidrosis patient, a gradient of concentration between the initial and the final time is calculated. Then, for the same hyperhidrosis patient, at a time where the temperature is T=24° C. and the relative humidity is RH=50%, a gradient of concentration between the final and initial time is calculated. This last gradient along with the first one are mathematically manipulated with the factor Fenv to obtain the perspiration level evolution through time despite modifications in environmental conditions. This mathematical manipulation is then compared to a table which associates each level of severity to a range of concentration gradients. The same is performed for specific humidity. Then, the concentration gradient associated to this mathematical manipulation and the corresponding auto-control measure are compared and the increase, decrease or stagnation of those values are interpreted by the healthcare professionals.

Accordingly, the following equations are stored in the memory of the system controller and performed thereby via computer-implementable steps:

$$\Delta C_{control} = C_{f\_int\_c} \quad C_{i\_int\_c}$$

$$\Delta C_{control} = C_{f_{int_c}}\left(RH_{f_{int}}; T_{f_{int}}\right) \quad C_{i_{int_c}}\left(RH_{i_{int}}; T_{i_{int}}\right)$$

$$\Delta C_{evaluation} = (\Delta C_{control}) \quad F_{env,C}$$

Wherein $C_{i\_int\_c}$ represents the average internal molecular water concentration at the initial time for a specific combination of temperature $T_{i_{int}}$, and relative humidity $RH_{i_{int}}$. Wherein to obtain the average in an initial time all measurements are performed within the same measuring session.

Wherein $C_{f\_int\_c}$ represents the average internal molecular water concentration at the final time for a specific combination of temperature $T_{f_{int}}$ and relative humidity $RH_{f_{int}}$. Wherein to obtain the average in an initial time all measurements are performed within the same measuring session.

Wherein $\Delta C_{control}$ represents the internal molecular water concentration gradient from the average internal molecular water concentrations for a specific combination of temperature and relative humidity at the initial and final times (or time stamps).

Wherein $\Delta C_{evaluation}$ represents the internal molecular water concentration gradient transposed, with an environmental factor $F_{env,C}$, from the average internal molecular water concentrations, for a specific combination of temperature and relative humidity at the initial and final times, to a comparative value used in the severity scale.

Figure 7:
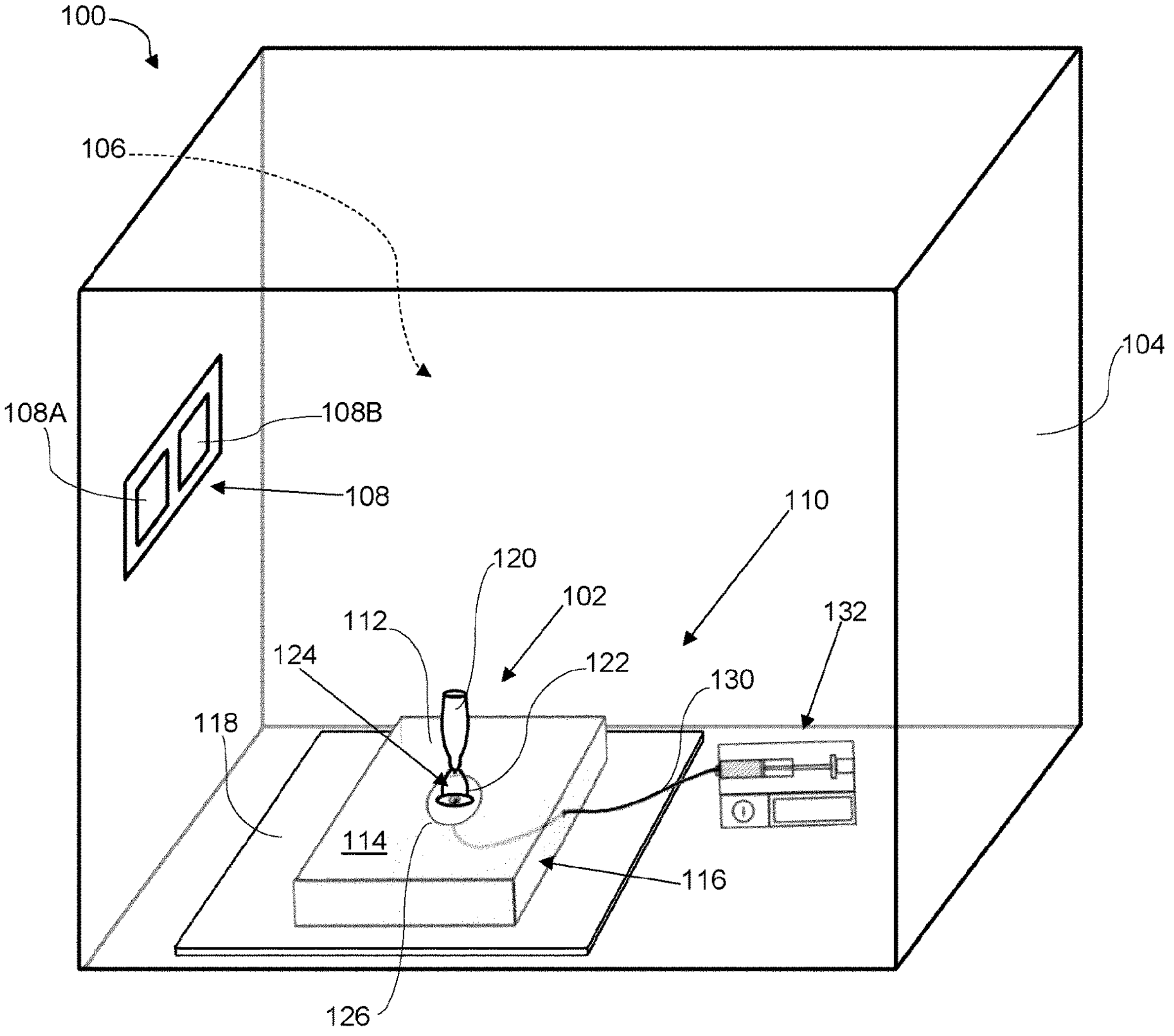
FIG. 7 is a schematic representation of a device for capturing, collecting and measuring a sweat sample on a skin surface of a subject in accordance with a non-limiting illustrative embodiment of the present disclosure within an environmental control testing system.
Figure 8:
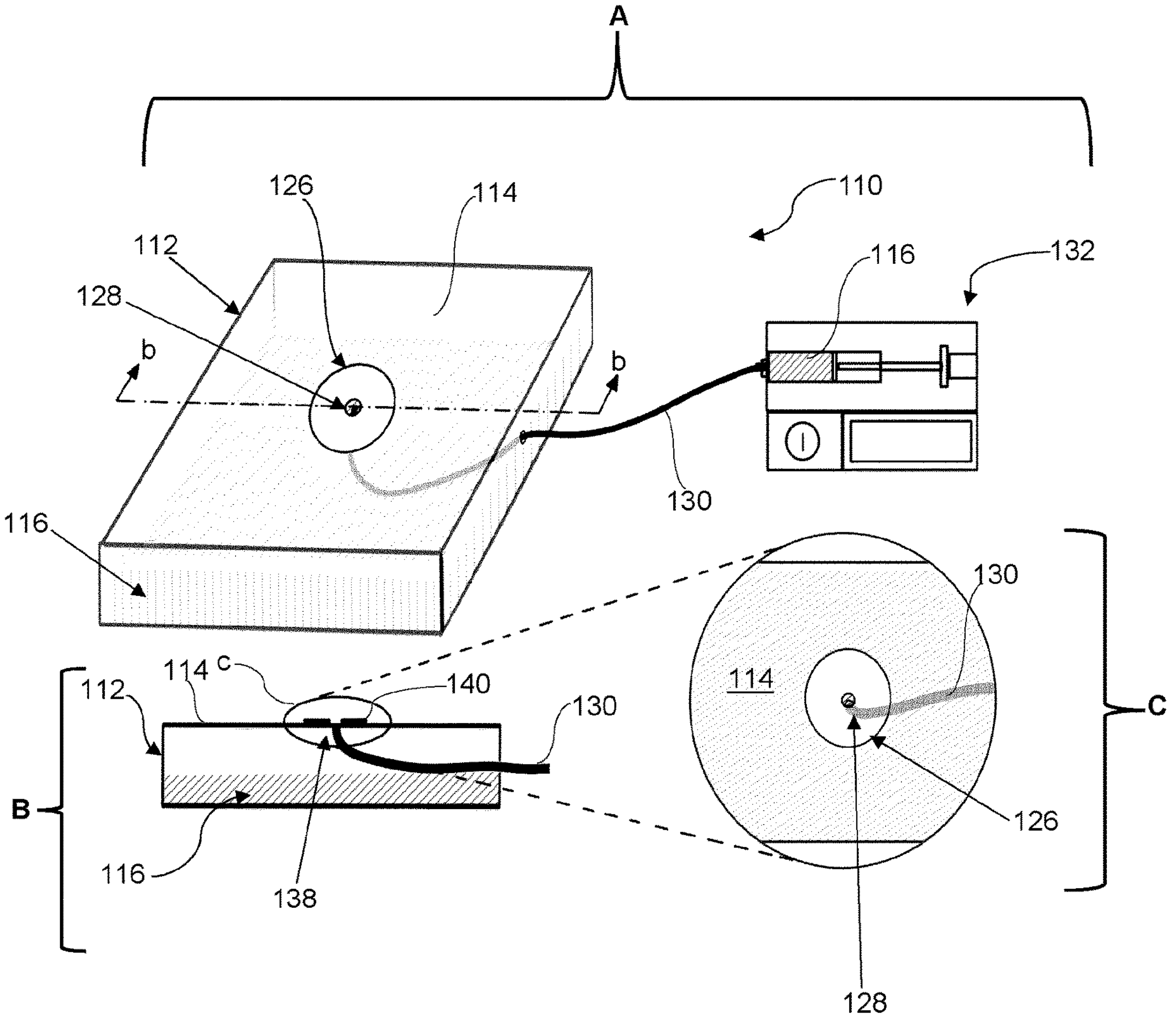
FIG. 8 is a schematic representation of components of the environmental control testing system including figure parts A, B and C, wherein figure part B is a sectional view of portion A taken along lines b-b of figure part A, and figure part C being an enlarged view of portion c of figure part B.

Turning to FIGS. 7 and 8, there is shown environmental control testing system 100 for running tests on a device 102 for capturing, collecting and measuring a sweat sample on a skin surface of a subject in accordance with a non-limiting illustrative embodiment of the present disclosure.

With particular reference to FIG. 7, the system 100 comprises an environmental control enclosure or cage 104 for providing a controlled environment 106 therein, wherein relative humidity and temperature are controlled. The cage 104 includes a control window 108 to observe and control the temperature and relative humidity parameters. Window portion 108A and 108B are linked to respective internal temperature and relative humidity sensors as will be understood by the skilled artisan. The device 102 is positioned within the cage 104 and subject to the controlled environment 106. The device 102 is positioned on a subject simulator assembly 110.

With respect to both FIGS. 7 and 8, the subject simulator assembly 110 emulates the perspiring skin surface a subject. The assembly 110 comprises a box 112, particularly a flat plastic hollow box having a flat top surface 114 (emulating the skin surface) and containing water 116 therein. About half the box 112 is filled with water 116. The box 112 is positioned on a heated pad 118. The device 102 comprises a handle 120 and a dome shaped sweat collecting and capturing body 122. The dome shaped body 122 is positioned on the flat top surface 114 forming a chamber 124 therewith as was previously explained when the device sweat collecting and capturing body engages the subject's skin surface. The heated pad 118 heats the water 116 within the box 112 thereby providing conditions similar to the skin temperature of a human hand for example. A circular contact region 126 is identified on the top surface 114 of the box 112. This contact region 126 is engaged by the dome shaped body 122 and represents the testing zone which includes a small aperture 128. A hose 130 connected at one end thereof to a syringe pump 132 runs through a side 134 of the box 112 via a small hole 136 with its other hose end 138 being positioned through the aperture 128 and being contiguous with flanges 140 in the zone 126 which are flush with the top surface 114. In this way, water 116 from the syringe pump 132 is pumped via the hose 130 running through the box 112 to leak out at end 138 via aperture 128 onto the top surface 114 thereby emulating perspiration. Accordingly, the rate of perspiration (water flow on top surface 114) can be controlled.

Experimental testing was performed in a controlled environment as provided by the testing system 10 in order to assess the accuracy of the device 102 and the environmental impact on the measured data. The aim of this experiment was to reproduce to the best of our knowledge the setup that would be used during the use of the device 102 by medical professionals. Moreover, the patient (subject) needed to be represented as well. However, due to the unique character of every human being, the patient was represented in a simple way so that the experiment could be reproducible. The following requirements were considered. To mimic the perspiration rate, the injection of a controlled liquid flow similar to that of sweat glands in terms of accuracy and limits would be required. To represent it, a syringe pump 132 with a controlled flow rate was used to represent the perspiration rate as accurately as possible in a simulated context. To determine the flow rates to be used during the experiment so that they would be the close to the sweat glands' actual excretion rates in different situations, a literature review was performed to isolate the most frequently measured flow rates during clinical experimentation. Two types of populations were observed in those articles: a control population (healthy) and a hyperhidrotic population. The minimal flow rates measured in these populations were 10 $ml/m^2$ and 70 $ml/m^2$ respectively and the maximal flow rates measured were 200 $ml/m^2$ and 2000 $ml/m^2$ respectively. To apply these values within the experiment of the disclosure, the patient/subject was represented by a flat plastic box 112 with a delimited circular zone 126 with flanges 140 containing a water outlet or aperture 128 in its center to mimic the perspiration output.

It should be noted that every molecular concentration regarding this experiment using system 10 is written considering the following unit: $\times \mathbf{10}^{17}$ $molecules/m^3$ Moreover, to continue representing the patient accurately within the experimental domain, the top surface 114 of the box 112, which represents the skin, was set at skin temperature (~30-35° C.) (Chan, L. M., Seon-Pil, J., Eun, D. J., Dong, L. H., & Jin, C. H. (2019). Regional Variation of Human Skin Surface Temperature. Annals of Dermatology, 3(31), 349-352). To achieve this, a heating pad 118 was placed underneath the box 112 and the box 112 was filled with water 116 so that the heat would propagate while rising and dissipate at the surface 114 to obtain a temperature close to that of the skin on the surface: 34-34.5° C. The liquid used to mimic perspiration rates had to be close in composition to that of sweat; therefore, tap water was used because of its ions' concentrations close to the ions' concentration in perspiration. The diffusion methods for this liquid had to be similar to that of sweat through the skin (via a secretory coil) and to that of sweat on the surface of the skin (via the pores). Therefore, to diffuse the liquid, a flexible tube or hose 130 was used to represent the secretory coil and the pore outlet. The sealing of the tube on the surface 114 of the box 112 was made with aquatic silicone.

To standardize the measurement, the surrounding environment parameters had to be controlled. Thus, an environmental control cage 104 connected to temperature and humidity sensors to adjust continuously the temperature and humidity was created.

The process of measurement was performed in two different typical environments meant to replicate the clinical environment in which the device 102 is used during two seasons of the year: summer and winter. The temperature and relative humidity measures were taken with a calibrated sensor. The first environmental conditions corresponding to winter conditions are: RH (Relative Humidity): 35%+−5%; T (Temperature): 22.5° C.+−0.5° C. The second environmental conditions corresponding to winter conditions are: RH: 50%+−5%; T: 24° C.+−0.5° C. For each test, a data chain of 60 values was taken for a period of 44 seconds. For each environment, measures were taken for two representative rates and ten data chains each.

The outlet surface 114 of the box delimited 126 for these measures is 58 $cm^2$. The measured flow rates are 10 ml/h and 25 ml/h which corresponds to 1724 ml/h·m^2 and 4310 ml/h·m^2 within the experimental surface used in this instance. It was decided to evaluate the accuracy of the device 102 for those rates in order to evaluate the lowest obtainable accuracy. Indeed, the higher the rate the more water 116 is sent to the experimental zone 126 under the device's experimental chamber 124. However, with more water 116 being accumulated, the evaporation rate progressively decreases (because less of the water 116 is in contact with the air) thereby increasingly saturating the sensor which negatively affects its accuracy. Therefore, it is better to evaluate the device 102 accuracy by evaluating it at the highest sweat rates which would represent the lower limit of the device's accuracy range. For the lowest rates, the measurement would be taken during conditions of high evaporation rates and therefore, the sensor would not tend to be saturated. Consequently, the accuracy of the sensor will reflect the accuracy of the device 102 and will be the upper limit of the device's accuracy.

Device Accuracy

The device 102 accuracy is measured by calculating the error on measures that considers the sample size. In order to calculate the errors, the standard deviation between the different measures taken on the testing apparatus is calculated. The error on measures is calculated according to the following formula for both of the flow rates.

Formula to Calculate the Error:

$$Err = \frac{\sigma}{\sqrt{n-1}};$$

σ=standard deviation; n=sample size

Environmental Conditions #1

RH: 35%+−5%; T: 22.5° C.+−0.5° C.

TABLE 6

Device's accuracy on measure in the environmental conditions #1 for two distinct flow rates

| Flow (ml/h) | Sample size (number of tests) | Error (%) | Device's accuracy (%) |
|---|---|---|---|
| 25 | 10 | 3.55 | 96.45 |
| 10 | 10 | 2.55 | 97.45 |

Environmental Conditions #2

RH: 50%+−5%; T: 24° C.+−0.5° C.

TABLE 7

Device's accuracy on measure in the environmental conditions #2 for two distinct flow rates

| Flow (ml/h) | Sample size (number of tests) | Error (%) | Device's accuracy (%) |
|---|---|---|---|
| 25 | 10 | 5.65 | 94.45 |
| 10 | 10 | 2.38 | 97.62 |

As shown above, measurement errors increase with the increasing rate. Therefore, for the maximum rate included between 10 ml/h and 25 ml/h, a maximal error of 5.65% can be observed which is highly acceptable. Moreover, close to the maximal measures, a maximal error of 2.38% can be observed which is also highly acceptable. Indeed, hyperhidrosis is a non-life-threatening disease that affects only 5% of the population; therefore, a minimal accuracy of 94.45% is considered highly acceptable. Hence, the device's accuracy is estimated to be sufficient to establish a good diagnosis based on its measures.

Environmental Influence

Considering the measures taken for each flow in the two different environments, the influence of the external environment on the measurement can be evaluated. The difference between the measures of concentration in the two environments is calculated. Then, the diminution of one from the other is determined. The diminution percentage is then calculated to establish the impact of the environment on our measure. Finally, a ratio of the winter value and the summer value is calculated in order to determine the environmental factor to use to evaluate a summer value compared to a winter value and vice versa.

TABLE 8

Device's measures of molecular concentration gradient in the two environmental conditions for two distinct flow rates

| | Range of molecular concentration | |
|---|---|---|
| Environmental conditions | 10 ml/h | 25 ml/h |
| [22.5° C. +− 0.5° C., 35% +− 5%] | 0.252 | 0.519 |
| [24° C. +− 0.5° C., 50% +− 5%] | 0.106 | 0.215 |

TABLE 9

Difference of the device's measures of molecular concentration gradient between the two environmental conditions for two distinct flow rates

| | 10 ml/h | 25 ml/h |
|---|---|---|
| Difference of concentration between the two environmental conditions (summer − winter) | −0.146 | −0.304 |

TABLE 9-continued

| Difference of the device's measures of molecular concentration gradient between the two environmental conditions for two distinct flow rates | | |
|---|---|---|
| | 10 ml/h | 25 ml/h |
| Diminution percentage between environmental conditions #1 et #2 | 58% | 59% |

TABLE 10

| Ratio of the device's measures of molecular concentration gradient in the two environmental conditions for two distinct flow rates to evaluate the impact of summer season on the measures | | |
|---|---|---|
| | 10 ml/h | 25 ml/h |
| Ratio of the concentrations (summer/winter) | $\frac{0.106}{0.252} = 0.421$ | $\frac{0.215}{0.519} = 0.414$ |

It should be noted that 10 ml/h and 25 ml/h are the closest rates to the human normal and hyperhidrotic sweat rates for the surface on which the tests are realized.

The average of the two concentrations' ratios previously calculated is determined as the potential environmental factor to transpose a winter value into a summer value: Potential environmental factor (winter to summer values): ×0.418.

The inverse of the average of the concentrations' ratios therefore corresponds to the potential environmental factor to transpose a summer to a winter value: Potential environmental factor (summer to winter values): ×2.39

In an example involving a healthcare professional in a North American clinical facility during a random month, if the month is included between November to March, it would be considered to belong to the winter season; if the month is included between April to October, it would be considered to belong to the summer season. In an example involving a healthcare professional in another clinical facility from another geographic region, the winter season would correspond to months associated with wintertime in this specific region. Correspondingly, the summer season would correspond to months associated with summertime in this specific region. In one example, after performing a test and extracting a concentration value, the healthcare professional should also annotate the season during which they performed the test, for example the summer season. Indeed, during the following session, for example in the winter season, the healthcare professional can transpose any previously taken values that were taken in another season (here, the summer season) by modulating them with the corresponding environmental factor. The now transposed historical values can then be accurately compared to the most recent value, here taken in the winter season. If the transposed measure and the most recent measure differ, it can be explained by multiple reasons:

(i) If the new measure is lower than the transposed measure, it can mean that the treatments the patient has been performing are efficient.

(ii) If the new measure is higher than the transposed measure, it can mean that the hyperhidrosis of the patient has worsened.

(iii) If the new measure is the same as the modified measure, it can mean that the patient's hyperhidrosis is unchanged.

Hence, the environmental factors provide for establishing the effect of the environment on the device's measure. Therefore, it can be used by the healthcare professional to study more accurately the evolution of the patients' hyperhidrosis levels and to refine the patient's diagnosis in respect to the intrinsic yet significant variability of the values according to the environmental conditions.

Severity Scale (Based on a Small Sample, 23)

In one example, the system 100 was used to conduct measurements to assess the severity level of hyperhidrosis of patients. A sample of 23 subjects was evaluated containing patients with diverse assumed levels of hyperhidrosis all working in a company that sells hyperhidrosis treatment devices. The subjects' concentration gradients were measured multiple times and the average concentration gradient for each patient was calculated. The different levels of hyperhidrosis of the scale used in this example are qualitatively corresponding to:

TABLE 11

| Qualitative evaluation of hyperhidrosis's levels based on the patient's perception and the esthetical aspect of his hands according to the observator | | |
|---|---|---|
| Hyperhidrosis severity level | Patient's perception | Patient's hands' aspect according to the observer |
| 0 | My sweating is never noticeable and never interferes with my daily activities | Dry/Normal hands |
| 1 | My sweating is noticeable but rarely interferes with my daily activities | Humid hands |
| 2 | My sweating is tolerable and sometimes interferes with my daily activities | Wet hands |
| 3 | My sweating is barely tolerable and frequently interferes with my daily activities | Soaked and dripping |
| 4 | My sweating is intolerable and always interferes with my daily activities | Soaked and pouring hands |

In one example, every patient's measurements were assessed in a moderately controlled environment. The molecular concentration was measured with the system described herein. For each severity level qualitatively described above, a range of molecular concentrations including all the patients considered in those levels was established. The ranges are described below:

TABLE 12

| Quantitative evaluation of hyperhidrosis' severity levels depending on the molecular concentration gradient | |
|---|---|
| Hyperhidrosis severity level | Range of molecular concentration gradient |
| 0 | 0-1.6 |
| 1 | 1.6-2.5 |
| 2 | 2.5-3 |
| 3 | 3-3.4 |
| 4 | 3.4+ |

Moreover, an epidemiological study for the sample used was conducted and compared to the traditional distribution of a sick population. For a sample of 23 patients, the severity level was assessed qualitatively according to Table 6; and quantitatively according to Table 7. The two assessments for each patient were noted in Table 8 and an error percentage of 13.6% was determined. This percentage, although it is low, can be explained by the small size of the sample and also by the small number of measures considered in the calculation of the average concentration gradients. Table 13 shows the comparison between the two types of assessments:

TABLE 13

Comparison of the qualitative and quantitative diagnosis for a sample of 23 patients

| Patient's ID number | Qualitative - Severity Level | Average Concentration Gradient | Qualitative - Severity level | Error between qualitative and quantitative assessment |
|---|---|---|---|---|
| 1 | 0 | 1.196 | 0 | 0.136 |
| 2 | 0 | 0.29 | 0 | |
| 3 | 1 | 2.29 | 1 | |
| 4 | 0 | 0.6 | 0 | |
| 5 | 2 | 2.84 | 2 | |
| 6 | 2 | 0.9 | 0 | |
| 7 | 1 | 2.02 | 1 | |
| 8 | 1 | 2.11 | 1 | |
| 9 | 1 | 2.17 | 1 | |
| 10 | 2 | 1.84 | 1 | |
| 11 | 2 | 2.67 | 2 | |
| 12 | 1 | 1.12 | 0 | |
| 13 | 1 | 1.73 | 1 | |
| 14 | 1 | 1.48 | 0 | |
| 15 | 3 | 3.2 | 3 | |
| 16 | 0 | 0.61 | 0 | |
| 17 | 2 | 2.5 | 2 | |
| 18 | 0 | 1.18 0 | 0 | |
| 19 | 2 | 2.88 | 2 | |
| 20 | 0 | 1.34 | 0 | |
| 21 | 2 | 2.8 | 2 | |
| 22 | 0 | 1.4 | 0 | |
| 23 | 0 | 0.9 | 0 | |

The following occurrences were measured for each severity level:

TABLE 14

Prevalence of levels in a sample of 23 patients

| Severity Scale | Occurrence | Prevalence of levels (%) |
|---|---|---|
| 0 | 11 | 47.82608696 |
| 1 | 6 | 26.08695652 |
| 2 | 5 | 21.73913043 |
| 3 | 1 | 4.347826087 |
| 4 | 0 | 0 |
| Sum | 23 | 100 |

The high prevalence of level 1 and 2 compared to a traditional distribution of a diseased population can be explained by a higher proportion of people with hyperhidrosis in a company that sells hyperhidrosis treatment devices.

Influence of Lifestyle

In another example, the lifestyle of the subjects would potentially impact the measures of water's concentration gradient. Consequently, the food habits and the intensity and frequency of sport practice are considered. A high frequency of sport practice can enhance the perspiration rhythm but also a really low one. Spicier foods tend to increase the perspiration rhythm; processed foods also. Therefore, a lifestyle factor could be included in the algorithm directly in the system. It could also be given separately to the healthcare professionals to allow them to choose whether or not to include it.

Influence of Body Temperature

In another example, the body temperature of the subjects would potentially impact the measures of water's concentration gradient. Consequently, the skin's temperature is considered as a factor. High body temperature would increase the sweating naturally so that the body can cool down. In addition to hyperhidrosis' related sweating, this sweating resulting from a higher body temperature than usual could alter the data by increasing it without relation to hyperhidrosis. Therefore, a body temperature factor could be included in the algorithm directly in the system. It could also be given separately to the healthcare professionals to allow them to choose whether or not to include it.

It is noted that one or more, or all, or any combination of the equations provided herein being stored within the memory of the controller, the controller implementable steps comprising executing the stored equations. It is also noted that one, or more, or all, or any combination of the above comparative or correspondence tables are stored within the memory of the controller, the controller implementable steps comprising identifying a correspondence between value entries as provided and explained hereinabove. It is further noted that one or more, or all, or any combination of the factors including the environmental factors are stored within the memory of the controller, the controller implementable steps comprising adjusting current readings to readings taken under other environmental conditions as provided herein.

The various features described herein can be combined in a variety of ways within the context of the present disclosure so as to provide still other embodiments. As such, the embodiments are not mutually exclusive. Moreover, the embodiments discussed herein need not include all of the features and elements illustrated and/or described and thus partial combinations of features can also be contemplated. Furthermore, embodiments with less features than those described can also be contemplated. It is to be understood that the present disclosure is not limited in its application to the details of construction and parts illustrated in the accompanying drawings and described hereinabove. The disclosure is capable of other embodiments and of being practiced in various ways. It is also to be understood that the phraseology or terminology used herein is for the purpose of description and not limitation. Hence, although the present disclosure has been provided hereinabove by way of non-restrictive illustrative embodiments thereof, it can be modified, without departing from the scope, spirit and nature thereof and of the appended claims.

What is claimed is:

1. A device for diagnosing hyperhidrosis or for use in the diagnosis of hyperhidrosis comprising:

a sweat capturing and collecting body forming a cavity therein and defining an opening leading to the cavity and being circumscribed by a contact surface for engaging the skin surface, wherein engagement of the skin surface by the contact surface provides for sealing the cavity thereby forming a chamber for capturing and collecting the sweat sample;

an internal humidity sensor positioned within the cavity for measuring internal humidity within the chamber which corresponds to a sweat rate measurement;

an internal temperature sensor positioned within the cavity for measuring internal temperature within the chamber which corresponds to a skin temperature measurement;

an ambient humidity sensor for measuring ambient humidity in an ambient environment to the skin;

an ambient temperature sensor for measuring ambient temperature in an ambient environment to the skin;

a user interface;

a controller in operative communication with the internal humidity sensor, the internal temperature sensor, the ambient humidity sensor, the ambient temperature sensor, and the user interface, the controller comprising a memory of controller executable code that when executed provides the controller with performing controller executable steps comprising:

receiving the measured internal humidity within the chamber from the internal humidity sensor at an initial time stamp and at a final time stamp;

receiving the measured internal temperature within the chamber from the internal temperature sensor at the initial time stamp and the final time stamp;

determining an initial molecular concentration of water in the air of the chamber at the initial time stamp and a final molecular concentration of water in air of the chamber at the final time stamp based on the internal humidity and internal temperature at the initial time stamp and the final time stamp respectively by performing calculations steps stored within the memory;

determining a molecular concentration gradient between the initial and final molecular concentrations of water in the air of the chamber;

receiving the measured ambient humidity from the ambient humidity sensor at the initial time stamp;

receiving the measured ambient temperature from the ambient temperature sensor at the initial time stamp;

modulating the internal molecular concentration gradient based on the ambient humidity and ambient temperature at the initial time stamp by performing modulation steps stored within the memory thereby determining a modulated molecular concentration gradient;

comparing the modulated molecular concentration gradient to a hyperhidrosis level and molecular concentration gradient correspondence table stored within the memory thereby determining a hyperhidrosis condition; and communicating the determined hyperhidrosis condition via the user interface.

2. A device according to claim 1, wherein the ambient humidity sensor is positioned externally to the chamber or within the cavity.

3. A device according to claim 1, wherein the ambient temperature sensor is positioned externally to the chamber or within the cavity.

4. A device according to claim 1, further comprising an atmospheric pressure sensor in operative communication with the controller for measuring atmospheric pressure, wherein the controller executable steps further comprise: receiving the measured atmospheric pressure, and wherein the analysis steps comprise modulating the molecular concentration gradient based on the measured atmospheric pressure.

5. A device according to claim 1, further comprising a heart rate sensor for measuring the heart rate of the subject and being in operative communication with the controller, wherein the controller executable steps further comprise: receiving the measured heart rate, and wherein the analysis steps comprise modulating the molecular concentration gradient based on the measured heart rate.

6. A device according to claim 1, further comprising a body temperature sensor for measuring the internal body temperature of the subject and being in operative communication with the controller, wherein the controller executable steps further comprise: receiving the measured internal body temperature, and wherein the analysis steps comprise modulating the molecular concentration gradient based on the measured internal body temperature.

7. A device for diagnosing hyperhidrosis or for use in the diagnosis of hyperhidrosis comprising:

a sweat capturing and collecting body forming a cavity therein and defining an opening leading to the cavity and being circumscribed by a contact surface for engaging the skin surface, wherein engagement of the skin surface by the contact surface provides for sealing the cavity thereby forming a chamber for capturing and collecting the sweat sample;

an internal humidity sensor positioned within the cavity for measuring internal humidity within the chamber which corresponds to a sweat rate measurement;

an internal temperature sensor positioned within the cavity for measuring internal temperature within the chamber which corresponds to a skin temperature measurement;

an ambient humidity sensor for measuring ambient humidity in an ambient environment to the skin;

an ambient temperature sensor for measuring ambient temperature in an ambient environment to the skin;

a user interface;

a controller in operative communication with the internal humidity sensor, the internal temperature sensor, the ambient humidity sensor, the ambient temperature sensor, and the user interface, the controller comprising a memory of controller executable code that when executed provides the controller with performing controller executable steps comprising:

receiving the measured internal humidity within the chamber from the internal humidity sensor at an initial time stamp and at a final time stamp;

receiving the measured internal temperature within the chamber from the internal temperature sensor at the initial time stamp and the final time stamp;

determining an initial specific humidity measurement in the chamber at the initial time stamp and a final specific humidity measurement in the chamber at the final time stamp based on the internal humidity and internal temperature at the initial time stamp and the final time stamp respectively by performing calculations steps stored within the memory;

determining a specific humidity gradient between the determined initial specific humidity and determined final specific humidity;

receiving the measured ambient humidity near the skin from the ambient humidity sensor at the initial time stamp;

receiving the measured ambient temperature near the skin from the ambient temperature sensor at the initial time stamp;

modulating the specific humidity gradient based on the ambient humidity and ambient temperature at the initial time stamp by performing modulation steps stored within the memory thereby determining a modulated specific humidity gradient;

comparing the modulated specific humidity gradient to a hyperhidrosis level and specific humidity gradient correspondence table stored within the memory thereby determining a hyperhidrosis condition; and communicating the determined hyperhidrosis condition via the user interface.

8. A device according to claim 7, wherein the ambient humidity sensor is positioned externally to the chamber or within the cavity.

9. A device according to claim 7, wherein the ambient temperature sensor is positioned externally to the chamber or within the cavity.

10. A device according to claim 7, further comprising an atmospheric pressure sensor in operative communication with the controller for measuring atmospheric pressure, wherein the controller executable steps further comprise: receiving the measured atmospheric pressure, and wherein the analysis steps comprise modulating the specific humidity gradient based on the measured atmospheric pressure.

11. A device according to claim 7, further comprising a heart rate sensor for measuring the heart rate of the subject and being in operative communication with the controller, wherein the controller executable steps further comprise: receiving the measured heart rate, and wherein the analysis steps comprises modulating the specific humidity gradient based on the measured heart rate.

12. A device according to claim 7 further comprising a body temperature sensor for measuring the internal body temperature of the subject and being in operative communication with the controller, wherein the controller executable steps further comprise: receiving the measured internal body temperature, and wherein the analysis steps comprise modulating the specific humidity gradient based on the measured internal body temperature.

13. A method of diagnosing hyperhidrosis or for use in the diagnosis of hyperhidrosis by capturing, collecting and measuring a sweat sample on a skin surface of a subject, the method comprising:

forming a sealed chamber on the skin surface for capturing and collecting the sweat sample;

measuring internal humidity within the chamber at an initial time stamp and at a final time stamp;

measuring internal temperature within the chamber at the initial time stamp and the final time stamp;

determining an initial molecular concentration of water in the air of the chamber at the initial time stamp and a final molecular concentration of water in air of the chamber at the final time stamp based on the internal humidity and internal temperature at the initial time stamp and the final time stamp respectively;

determining a molecular concentration gradient between the initial and final molecular concentrations of water in the air of the chamber;

measuring ambient humidity in an ambient environment to the skin at the initial time stamp;

measuring ambient temperature in an ambient environment to the skin at the initial time stamp;

modulating the internal molecular concentration gradient based on the ambient humidity and ambient temperature at the initial time stamp thereby determining a modulated molecular concentration gradient;

comparing the modulated molecular concentration gradient to a hyperhidrosis level and molecular concentration gradient correspondence table thereby determining a hyperhidrosis condition.

14. A method according to claim 13, further comprising measuring atmospheric pressure in an ambient environment to the skin surface, wherein modulating the internal molecular concentration gradient is based on the measured atmospheric pressure.

15. A method according to claim 13, further comprising measuring an additional parameter selected from the group consisting of:

a heart rate of the subject;

a body temperature of the subject;

a pH level in the chamber;

a volatile organic compound concentration in the chamber;

colorimetric analysis within the chamber;

a force on the skin surface; and any combination thereof;

wherein modulating the molecular concentration gradient is based on one or more of the additional parameters.

16. A method according to claim 13, further comprising:

recognizing a configuration and size of the chamber;

wherein modulating the molecular concentration gradient is based on the recognized configuration and size of the chamber.

17. A method according to claim 13, providing for evaluating hyperhidrosis variation over a period of time, the method comprising:

determining the modulated molecular concentration gradient at a first measuring session thereby providing a first modulated molecular concentration gradient;

determining the modulated molecular concentration gradient at a second measuring session thereby providing a second modulated molecular concentration gradient, wherein the first and second session are spaced apart over time during which environmental conditions changed of at least ±1% (ambient relative humidity and temperature);

wherein any two following measuring sessions can be classified as a first measuring session and second measuring session;

transposing a determined one of the two measuring gradient value to a transposed of the other measuring value by mathematically manipulating it by an environmental factor; and comparing the transposed modulated molecular concentration gradient to the untransposed modulated molecular concentration gradient to determine an increase, decrease or lack of variation thereof in the hyperhidrosis level.

18. A method of diagnosing hyperhidrosis or for use in the diagnosis of hyperhidrosis by capturing, collecting and measuring a sweat sample on a skin surface of a subject, the method comprising:

forming a sealed chamber on the skin surface for capturing and collecting the sweat sample;

measuring internal humidity within the chamber at an initial time stamp and at a final time stamp;

measuring internal temperature within the chamber at the initial time stamp and the final time stamp;

determining an initial specific humidity of the chamber at the initial time stamp and a final specific humidity of the chamber at the final time stamp based on the internal humidity and internal temperature at the initial time stamp and the final time stamp respectively;

determining a specific humidity gradient between the initial specific humidity and the final specific humidity;

measuring ambient humidity in an ambient environment to the skin at the initial time stamp;

measuring ambient temperature in an ambient environment to the skin at the initial time stamp;

modulating the specific humidity gradient based on the ambient humidity and ambient temperature at the initial time stamp thereby determining a modulated specific humidity gradient;

comparing the modulated specific humidity gradient to a hyperhidrosis level and specific humidity gradient correspondence table thereby determining a hyperhidrosis condition.

19. A method according to claim 18, further comprising measuring atmospheric pressure in an ambient environment to the skin surface, wherein modulating the internal specific humidity gradient is based on the measured atmospheric pressure.

20. A method according to claim 18, further comprising measuring an additional parameter selected from the group consisting of:

a heart rate of the subject;

a body temperature of the subject;

a pH level in the chamber;

a volatile organic compound concentration in the chamber;

colorimetric analysis within the chamber; and any combination thereof;

wherein modulating the specific humidity gradient is based on one or more of the additional parameters.

21. A method according to claim 18, further comprising:

recognizing a configuration and size of the chamber;

wherein modulating the specific humidity gradient is based on the recognized configuration and size of the chamber.

22. A method according to claim 18, providing for evaluating hyperhidrosis variation over a period of time, the method comprising:

determining the modulated specific humidity gradient at a first measuring session thereby providing a first modulated specific humidity gradient;

determining the modulated specific humidity gradient at a second measuring session thereby providing a second modulated specific humidity gradient, wherein the first and second session are spaced apart over time during which environmental conditions changed of at least ±1% (ambient relative humidity and temperature);

wherein any two following measuring sessions can be classified as a first measuring session and second measuring session;

transposing a determined one of the two measuring gradient value to a transposed of the other measuring value by mathematically manipulating it by an environmental factor; and comparing the transposed modulated specific humidity gradient to the untransposed modulated specific humidity gradient to determine an increase, decrease or lack of variation thereof in the hyperhidrosis level.

* * * * *